(12) United States Patent
Chau et al.

(10) Patent No.: US 9,314,421 B2
(45) Date of Patent: Apr. 19, 2016

(54) ULTRASOUND-ENHANCED INTRASCLERAL DELIVERY OF MACROMOLECULES

(75) Inventors: Ying Chau, Hong Kong (CN); Chi Yeung Cheung, Hong Kong (CN); Yu Yu, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 763 days.

(21) Appl. No.: 12/717,180

(22) Filed: Mar. 4, 2010

(65) Prior Publication Data

US 2010/0226971 A1 Sep. 9, 2010

Related U.S. Application Data

(60) Provisional application No. 61/202,512, filed on Mar. 6, 2009.

(51) Int. Cl.

| | | |
|---|---|---|
| A61K 9/127 | (2006.01) | |
| A61K 9/14 | (2006.01) | |
| A61K 39/395 | (2006.01) | |
| A61P 27/02 | (2006.01) | |
| A61M 37/00 | (2006.01) | |
| A61K 9/00 | (2006.01) | |
| A61F 9/00 | (2006.01) | |

(52) U.S. Cl.
CPC .............. *A61K 9/0009* (2013.01); *A61F 9/0017* (2013.01); *A61K 9/0048* (2013.01); *A61M 37/0092* (2013.01)

(58) Field of Classification Search
None
See application file for complete search history.

(56) References Cited

U.S. PATENT DOCUMENTS

| | | | | |
|---|---|---|---|---|
| 5,617,851 A | * | 4/1997 | Lipkovker | ..................... 600/573 |
| 6,234,990 B1 | * | 5/2001 | Rowe et al. | ...................... 604/22 |
| 6,378,526 B1 | * | 4/2002 | Bowman et al. | .............. 128/898 |
| 6,491,657 B2 | * | 12/2002 | Rowe et al. | ...................... 604/22 |
| 2008/0177220 A1 | * | 7/2008 | Lindgren et al. | ................. 604/22 |

FOREIGN PATENT DOCUMENTS

WO    WO 2007081750 A2 * 7/2007

OTHER PUBLICATIONS

Park, J. et al. (2005). Evaluation of coupled convective-diffusive transport of drugs administered by intravitreal injection and controlled release implant. *Journal of Controlled Release*, 105: 279-295.
Chrai, S. S. et al. (1974). Drop size and initial dosing frequency problems of topically applied ophthalmic drugs. *Journal of Pharmaceutical Sciences*, 63(3): 333-338.
Sieg, J. W. & Robinson, J. R. (1976). Mechanistic studies on transcorneal permeation of pilocarpine. *Journal of Pharmaceutical Sciences*, 65(12): 1816-1822.
Schoenwald, R. D. et al. (1997). Penetration into the anterior chamber via the conjunctival/scleral pathway. *Journal of Ocular Pharmacology and Therapeutics*, 13(1): 41-59.
Maurice, D. M. (2002). Drug delivery to the posterior segment from drops. *Survey of Ophthalmology*, 47(Supplement 1): S41-S52.
Ambati, J. et al. (2000). Diffusion of high molecular weight compounds through sclera. *Investigative Ophthalmology & Visual Science*, 41(5): 1181-1185.
Ranta, V-P & Urtti, A. (2006). Transscleral drug delivery to the posterior eye: Prospects of pharmacokinetic modeling. *Advanced Drug Delivery Reviews*, 58: 1164-1181.
Urtti, A. (2006). Challenges and obstacles of ocular pharmacokinetics and drug delivery. *Advanced Drug Delivery Reviews*, 58: 1131-1135.
Mitragotri, S. et al. (1995). Ultrasound-mediated transdermal protein delivery. *Science*, 269(5225): 850-853.
Katz, N. P. et al. (2004). Rapid onset of cutaneous anesthesia with EMLA cream after pretreatment with a new ultrasound-emitting device. *Anesthesia and Analgesia*, 98: 371-376.
Santoianni, P. et al. (2004). Intradermal drug delivery by low frequency sonophoresis (25 KHz). *Dermatology Online Journal*, 10(2): 24-31.
Zderic, V. et al. (2002). Ocular drug delivery using 20-kHz ultrasound. *Ultrasound in Medicine and Biology*, 28(6): 823-829.
Zderic, V. et al. (2004). Drug delivery into the eye with the use of ultrasound. *Journal of Ultrasound in Medicine*, 23: 1349-1359.
Zderic, V. et al. (2004). Ultrasound-enhanced transcorneal drug delivery. *Cornea*, 23(8): 804-811.
Lee, V. H. L. & Robinson, J. R. (1986). Review: Topical ocular drug delivery: Recent developments and future challenges. *Journal of Ocular Pharmacology*, 2(1): 67-108.
Geroski, D. H. & Edelhauser, H. F. (2001). Transscleral drug delivery for posterior segment disease. *Advanced Drug Delivery Reviews*, 52(1): 37-48.
Myles, M. E. et al. (2005). Recent progress in ocular drug delivery for posterior segment disease: Emphasis on transscleral iontophoresis. *Advanced Drug Delivery Reviews*, 57(14): 2063-2079.
Janoria, K. G. et al. (2007). Novel approaches to retinal drug delivery. *Expert Opinion on Drug Delivery*, 4(4): 371-388.
Mitragotri, S. & Kost, J. (2004). Low-frequency sonophoresis: A review. *Advanced Drug Delivery Reviews*, 56(5): 589-601.
Kourlas, H. & Abrams, P. (2007). Ranibizumab for the treatment of neovascular age-related macular degeneration: A review. *Clinical Therapeutics*, 29(9): 1850-1861.
Zarbin, M. & Szirth, B. (2007). Current treatment of age-related macular degeneration. *Optometry and Vision Science*, 84(7): E559-E572.

(Continued)

*Primary Examiner* — Susan Tran
*Assistant Examiner* — William Craigo
(74) *Attorney, Agent, or Firm* — Saliwanchik, Lloyd & Eisenschenk

(57) ABSTRACT

The present invention provides a novel system and method for transscleral delivery of therapeutic agents, including macromolecules, into a target site in intrascleral space using ultrasound. Advantageously, the present invention not only significantly enhances transscleral diffusivity of macromolecular therapeutic agents, but also causes little damages to ocular tissues and structure.

19 Claims, 14 Drawing Sheets
(12 of 14 Drawing Sheet(s) Filed in Color)

(56) References Cited

OTHER PUBLICATIONS

Sieving, P. A. et al. (2006). Ciliary neurotrophic factor (CNTF) for human retinal degeneration: Phase I trial of CNTF delivered by encapsulated cell intraocular implants. *Proceedings of the National Academy of Sciences of the United States of America*, 103(10): 3896-3901.

Jiang, J. et al. (2009). Intrascleral drug delivery to the eye using hollow microneedles. *Pharmaceutical Research*, 26(2): 395-403.

Barza, M. et al. (1986). Transscleral iontophoresis of Cefazolin, Ticarcillin, and Gentamicin in the rabbit. *Ophthalmology*, 93(1): 133-139.

Maurice, D. M. (1986). Iontophoresis of Fluorescein into the posterior segment of the rabbit eye. *Ophthalmology*, 93(1): 128-132.

Barza, M. et al. (1987). Transscleral iontophoresis of Gentamicin in monkeys. *Investigative Ophthalmology & Visual Science*, 28(6): 1033-1036.

Asahara, T. et al. (2001). Induction of genes into the rabbit eye by iontophoresis. *Japanese Journal of Ophthalmology*, 45(1): 31-39.

Voigt, M. et al. (2002). Down-regulation of NOSII gene expression by iontophoresis of anti-sense oligonucleotide in endotoxin-induced uveitis. *Biochemical and Biophysical Research Communications*, 295: 336-341.

Parkinson, T. M. et al. (2003). Tolerance of ocular iontophoresis in healthy volunteers. *Journal of Ocular Pharmacology and Therapeutics*, 19(2): 145-151.

Kremer, F. B. et al. (1985). Determination of corneal thickness using ultrasonic pachometry. *Annals of Ophthalmology*, 17(8): 506-507.

McDermott, M. L. et al. (1997). Phacoemulsification for cataract following pars plana vitrectomy. *Ophthalmic Surgery and Lasers*, 28: 558-564.

Pavlin, C. J. et al. (1991). Clinical use of ultrasound biomicroscopy. *Ophthalmology*, 98(3): 287-295.

Saltzman, W. M. (2001). Drug Delivery: Engineering Principles for Drug Therapy; Chapter Three: Diffusion and Drug Dispersion. pp. 23-27. Oxford University Press: New York, NY.

Hamalainen, K. M. et al. (1997). Characterization of paracellular and aqueous penetration routes in cornea, conjunctiva, and sclera. *Investigative Ophthalmology & Visual Science*, 38(3): 627-634.

Edwards, A. & Prausnitz, M. R. (1998). Fiber matrix model of sclera and corneal stroma for drug delivery to the eye. *AIChE Journal*, 44(1): 214-225.

Kim, S. H. et al. (2007). Transport barriers in transscleral drug delivery for retinal diseases. *Ophthalmic Research*, 39: 244-254.

Merino, G. et al. (2003). Ultrasound-enhanced transdermal transport. *Journal of Pharmaceutical Sciences*, 92(6): 1125-1137.

Blinc, A. et al. (1993). Characterization of ultrasound-potentiated fibrinolysis in vitro. *Blood*, 81(10): 2636-2643.

Braaten, J. V. et al. (1997). Ultrasound reversibility disaggregates fibrin fibers. *Journal of Thrombosis and Haemostasis*, 78: 1063-1068.

Perren, F. et al. (2008). Microbubble potentiated transcranial duplex ultrasound enhances IV thrombolysis in acute stroke. *Journal of Thrombosis and Thrombolysis*, 25: 219-223.

Collis, J. et al. (2010). Cavitation microstreaming and stress fields created by microbubbles. *Ultrasonics*, 50: 273-279.

Kodama, T. & Tomita, Y. (2000). Cavitation bubble behavior and bubble-shock wave interaction near a gelatin surface as a study of in vivo bubble dynamics. *Applied Physics B*, 70: 139-149.

Qasim, M. A. & Salahuddin, A. (1979). The conformational consequences of maleylation of amino groups in ovalbumin. *Journal of Biochemistry*, 85(4): 1029-1035.

Watson, P. G. & Young, R. D. (2004). Scleral structure, organisation and disease: A review. *Experimental Eye Research*, 78: 609-623.

Hay, E. D. (1991). Cell biology of extracellular matrix. $2^{nd}$ Ed. Plenum Press: New York.

Yokoi, H. et al. (2005). Dynamic reassembly of peptide RADA16 nanofiber scaffold. *Proceedings of the National Academy of Sciences of the United States of America*, 102(24): 8414-8419.

Lavon, I. & Kost, J. (2004). Ultrasound and transdermal drug delivery. *Drug Discovery Today*, 9(15): 670-676.

U. S. Department of Health and Human Services et al. (1997). Guidance for Industry and FDA Staff: Information for Manufacturers Seeking Marketing Clearance of Diagnostic Ultrasound Systems and Transducers.

Cruysberg, L. P. J. et al. (2005). The influence of intraocular pressure on the transscleral diffusion of high-molecular-weight compounds. *Investigative Ophthalmology & Visual Science*, 46(10): 3790-3794.

\* cited by examiner

ULTRASOUND-ENHANCED INTRASCLERAL DELIVERY OF MACROMOLECULES

CROSS-REFERENCE TO RELATED APPLICATION

The subject application claims the benefit of U.S. Provisional Application Ser. No. 61/202,512, filed Mar. 6, 2009, which is incorporated herein by reference in its entirety.

BACKGROUND OF THE INVENTION

Although therapeutics for treating posterior segment eye diseases are emerging, the treatment of these diseases is limited to a significant extent by the difficulty of delivering effective dose of therapeutics to the target tissues. This is because the eye is a well-protected organ that possesses several barriers for deterring foreign substances from entering the posterior segment of the eye. In addition, many promising therapeutics for treating posterior segment eye diseases, such as PEGylated-aptamer (Macugen®) and antibody fragments (Lucentis®), have high molecular weight, and thus can hardly diffuse across the ocular tissues. Therefore, an effective, non-invasive method for delivering macromolecules to the posterior segment of the eye is needed.

Common routes for delivering ocular therapeutics to the posterior segment of the eye include: the intravitreal route, the systemic route, the transcorneal route, the periocular route, and the transscleral route. The intravitreal route, where therapeutic agents are directly injected into the vitreous of the eye, is the most direct and effective, but is also the most invasive route. In addition to the risk of damaging the ocular tissues, the mobility of large molecules, particular positively charged ones, is restricted in the vitreous. As a result, large molecules can hardly diffuse from the vitreous to the retina. (1) Furthermore, as multiple injections are frequently required, there is a risk of having cataract, retinal detachment, vitreous hemorrhage and endophthalmitis after treatment. (18)

Systemic delivery, another way to deliver drugs to the posterior segment, also has significant limitations. A large systemic dose is necessary to reach the therapeutic level because the blood-retinal barrier (BRB) largely decreases the flux of drugs to the retina. Undesirable side effects are resulted when a high concentration of therapeutics is distributed in the body via the circulation system. (16) In addition, emerging therapeutics such as proteins and nucleic acids may be degraded during systemic delivery before they reach the eye.

Topical application using eye drops takes the transcorneal route. Despite the ease of administration, drug delivery via this route has to overcome a number of difficult barriers and undertake a long path until drugs finally reach the posterior segment. Before entering the anterior segment, however, drug molecules may have already been eliminated by solution drainage, lacrimation and tear dilution, tear turnover, and conjunctival adsorption, or blocked by the tight junctions in the corneal epithelium. (2, 3) Even after reaching the anterior segment, therapeutics may still be removed by the intraocular tissues and fluids. The iridolenticular diaphragm and the aqueous humor flow would also prevent the therapeutics from entering the posterior segment. (4, 5) As a result, only 3% of the administered dose eventually enters the aqueous humor in the anterior segment, (15) and there is almost no therapeutics delivered into the posterior segment via the topical route.

Periocular injection is performed by injecting drugs in the periocular space of the eye. After injection, the drugs diffuse down their concentration gradient across the sclera into the posterior segment of the eye. One limitation of this approach is the difficulty of maintaining a high concentration gradient to deliver therapeutics into the eye. In addition, safety of periocular injection relies on high levels of medical skills. Further, as multiple injections are frequently needed for long-term treatment, the risk of retinal detachment, cataract formation and other ocular maladies increases. (17)

Transscleral route has attracted much interest as a potential path for delivering therapeutics into the posterior segment, because there are certain advantages: first, diffusion of macromolecules through the sclera is feasible, as demonstrated in the ex viva diffusion experiments using rabbit sclera by Ambati et al. (24) Second, the distance for drug molecules to penetrate into the posterior segment is shorter via the transscleral than the transcorneal route. After diffusing through the sclera, drug molecules are closer to the vicinity where most posterior diseases occur: the choroid and the retina.

In the transscleral route, the sclera is the first and outmost barrier. Although by passive diffusion, macromolecules like proteins are able to pass through the sclera (6), the permeability is low and the macromolecules can be easily washed away by tears or blood flow in the conjunctiva and the episclera. (7) As a result, the concentration gradient across the sclera and thus the flux of macromolecules into the intraocular tissue decreases dramatically.

A less invasive method has been developed by Jiang et al., using microneedles to deliver soluble molecules, nanoparticles and microparticles intrasclerally. (25) Using this approach, controlled drug release within the sclera was made possible by delivering drug-encapsulated nanoparticles and microparticles into the deeper sclera. Drug molecules could then diffuse to the neighboring posterior ocular tissues. Another technique, transscleral iontophoresis, has been employed by a number of research groups to deliver drugs to the posterior segment using electric field. (26-28) However, iontophoresis is limited to charged drugs. (17, 29, 20 Patients also complained about the burning sensation. (31) Another approach is scleral/intrascleral implant, which is capable of providing a prolonged therapeutic action, thereby solving the problem of multiple injections. However, one limitation is that implants require surgery and often cause discomfort.

Ultrasound, a longitudinal wave which has frequency above audible range, is a well-known technology in the medical field. It has been applied for diagnostic purposes, for example, for measuring the intraocular pressure of eye, and for therapeutic uses, for example, in healing muscle damage and in disrupting the lens in cataract surgery. Ultrasound, especially low-frequency ultrasound, has also been explored in enhancing drug delivery in transdermal route. It is found that the cavitation effect of the ultrasound would disrupt the outermost layer of the skin temperorily to increase the permeability of the skin. Mitragotri et al. has successfully delivered insulin and other protein molecules across human skin using low frequency ultrasound. (9) In clinical studies, methylprednisolone, cyclosporin and eutectic mixture of local anesthetics (EMLA) have been successfully delivered to produce significant therapeutic effects. (10, 11)

However, limited research has been performed to use ultrasound in ocular drug delivery. The most relevant research using ultrasound on ocular drug delivery is the ultrasound-mediated transconreal drug delivery. It has been discovered that ultrasound can enhance delivery of sodium fluorescein (a low molecular weight compound) through the cornea for ten times than passive diffusion. (12-14) To the best of our knowledge, none has investigated the effects of ultrasound in delivering macromolecules via the transscleral route.

The prior art of ocular drug delivery to the posterior segment of the eye is either ineffective or invasive and causes side effects. Therefore, a substantial need exists for a non-invasive, safer and more effective system and method for intrascleral delivery of macromolecules.

BRIEF SUMMARY OF THE INVENTION

The present invention provides a novel, non-invasive, safe and effective ultrasound-enhanced system and method for transscleral delivery of therapeutic agents, including macromolecules, into a target site in intrascleral space. Advantageously, the present invention significantly enhances transscleral diffusivity of macromolecular therapeutic agents, and is capable of delivering macromolecules having a molecular weight of up to about 150k Dalton. In addition, enhancement of drug delivery is repeatable. Further, the present invention applies low-intensity, low-frequency ultrasound, and thus causes little damages to ocular tissues and structure.

One aspect of the present invention provides an ultrasound-enhanced system for delivering therapeutic agents to a target site in intrascleral space. The system comprises: an ultrasound-generating device coupled with a well for transmitting and directing ultrasound to a desired site of the sclera. The ultrasound generated from the ultrasound-generating device creates cavitation, allowing the therapeutic agent to permeate across the desired site of the sclera to reach the target site in intrascleral space. In an embodiment, the ultrasound generating device is placed above or around the sclera at a distance of about 0.5 mm to about 5 mm. In another embodiment, the ultrasound is applied at a frequency of about 20 kHz to about 2.5 MHz. In another embodiment, the ultrasound is applied at a power of no greater than about 4 W/cm$^2$, preferably no greater than about 2 W/cm$^2$.

Another aspect of the present invention provides an ultrasound-enhanced method for delivering therapeutic agents to a target site in intrascleral space, comprising:
a) providing an ultrasound-generating device and a well for transmitting ultrasound;
b) positioning the ultrasound-generating device and the well so that ultrasound will be directed to a desired site of a sclera;
c) generating ultrasound using the ultrasound-generating device and applying the ultrasound to the desired site of the sclera; and
d) providing a therapeutic agent to the desired site of the sclera before, during, or after ultrasound is generated;
wherein the ultrasound-generating device is positioned at a distance of about 0.5 mm to about 5 mm above or around the desired site of the sclera;
wherein ultrasound creates cavitation allowing the therapeutic agent to permeate across the desired site of the sclera to reach the target site in intrascleral space; and
wherein the ultrasound has one or more of the following characteristics:
1) a frequency in the range of about 20 kHz to about 2.5 MHz; and
2) a power of no greater than about 4 W/cm$^2$, preferably no greater than about 2 W/cm$^2$.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
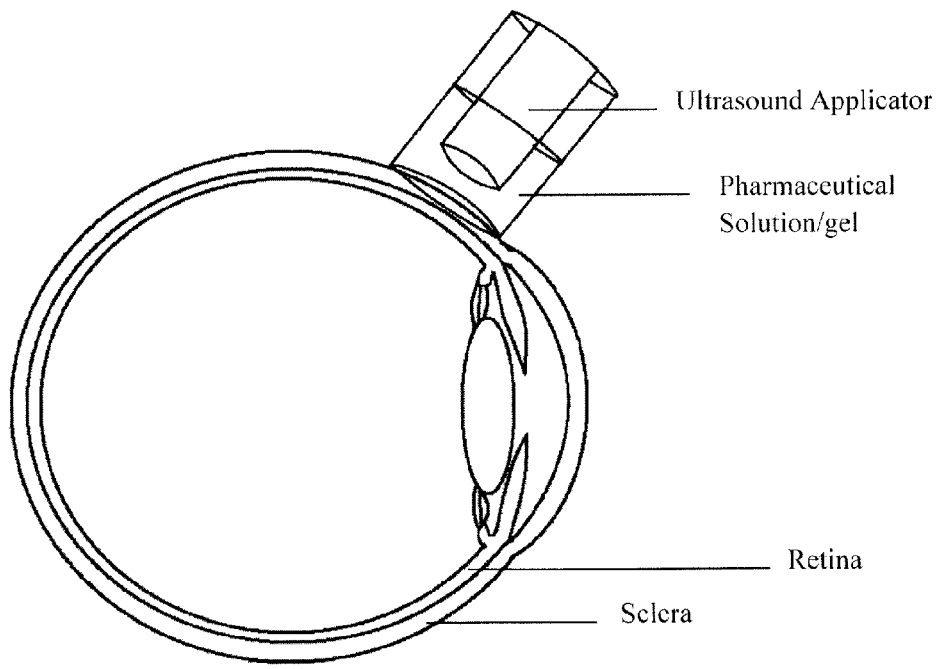
FIG. 1 is a schematic diagram illustrating the set up of an exemplified delivery system of the present invention. The ultrasound applicator is placed inside the well above the sclera.

This invention provides a novel and advantageous ultrasound-enhanced system and method for delivering therapeutic agents of macromolecular nature to the posterior segment of the eye. Specifically, the present invention utilizes the cavitation effect created by low to medium frequency ultrasound, which enables macromolecules to penetrate the sclera more effectively, whereby a sufficient dose can be placed in close proximity to the choroidal layer, where excessive neovascularization due to age-related macular degeneration and ocular trauma occurs. In addition, the present invention takes advantage of the depot effect by placing the therapeutic agents at the sclera and thus creates a higher flux to the intraocular tissues. Advantageously, the present invention significantly enhances transscleral diffusivity of macromolecular therapeutic agents, and is capable of delivering macromolecules having a molecular weight of up to about 150k Dalton. In addition, enhancement of drug delivery is repeatable. Further, the present invention applies low-intensity, low-frequency ultrasound, and thus causes little damages to ocular tissues and structure.

One aspect of the present invention provides a system for delivering therapeutic agents to a target site in intrascleral space using ultrasound. The system comprises: an ultrasound-generating device coupled with a well for transmitting and directing ultrasound to a desired site of the sclera. The ultrasound generated from the ultrasound-generating device creates cavitation, thereby allowing the therapeutic agent to permeate across the desired site of the sclera to reach the target site in intrascleral space. In an embodiment, the ultrasound generating device is placed above or around the sclera at a distance of about 0.5 mm to about 5 mm. In another embodiment, the ultrasound is applied at a frequency of about 20 kHz to about 2.5 MHz. In another embodiment, the ultrasound is applied at a power of no greater than about 4 W/cm$^2$, preferably no greater than about 2 W/cm$^2$.

Another aspect of the present invention provides a method for delivering therapeutic agents to a target site in intrascleral space, comprising:
 a) providing an ultrasound-generating device and a well for transmitting ultrasound;
 b) positioning the ultrasound-generating device and the well so that ultrasound will be directed to a desired site of a sclera;
 c) generating ultrasound using the ultrasound-generating device and applying the ultrasound to the desired site of the sclera; and
 d) providing a therapeutic agent to the desired site of the sclera before, during, or after ultrasound is generated; and
wherein the ultrasound-generating device is positioned at a distance of about 0.5 mm to about 5 mm above or around the desired site of the sclera;
wherein ultrasound creates cavitation allowing the therapeutic agent to permeate across the desired site of the sclera to reach the target site in intrascleral space; and
wherein the ultrasound has one or more of the following characteristics:
 1) a frequency of about 20 kHz to about 2.5 MHz; and
 2) a power of no greater than about 4 W/cm$^2$, preferably no greater than about 2 W/cm$^2$.

Sclera is an attractive portal for delivering macromolecular therapeutic molecules to the back of the eye since high molecular weight compounds, including dextrans, polyethylene glycols and globular proteins (24, 35, 26), are found to be permeable to this outermost barrier in the posterior segment. However, the episcleral clearance and the outward bulk fluid flow arising from osmotic or hydrostatic pressure decrease the amount of drugs that can be effectively delivered. Drug delivery is even more challenging for macromolecules, such as proteins and nucleic acids, because permeability through the sclera decreases exponentially with the molecular radius. (24, 36) To overcome these transport barriers, the intrascleral flux must be increased.

Thus, the present invention provides a safe, effective and non-invasive approach employing ultrasound to enhance the transscleral delivery of therapeutics. The application of low-frequency ultrasound for a short duration induces cavitation—the formation of bubbles by ultrasound waves (19). It is discovered that the cavitation effect can enhance transdermal drug delivery (39) and the acceleration of fibrinolysis (40). The violent collapse of bubbles and the subsequent release of energy, a phenomenon termed inertial cavitation, can be used to explain the augmented delivery of large and hydrophilic molecules through the skin by low-frequency ultrasound. In transient cavitation, the subsequent collapse of bubbles will create shock waves and/or microjects. The shock waves and/or microjets created by cavitation disrupt the lipid bilayer in the stratum corneum and generate aqueous transport pathways (39). In fibrinolysis, medium-frequency ultrasound is used to improve the transport of proteins including plasminogen into the blood clot. Microstreaming due to a stable oscillation of bubbles (non-inertial cavitation) has been proposed as the mechanism that reversibly changes the fiber structure in a fibrin gel, resulting in a drop of the resistance against protein transport (41-43).

Cavitation also allows the macromolecules to penetrate deeper into the sclera. The disruption creates temporary channels in the outermost sclera. These channels increase the permeability of the sclera temporarily, and thereby allowing delivery of therapeutic agents including macromolecules across the sclera. In stable cavitation, the oscillation of bubbles will cause microstreaming and create more gentle forces for disruption. In addition, the diffusion distance between the sclera and the choroid is decreased via intrascleral delivery. As a result, the intrascleral positioning of the macromolecules helps to avoid clearance by tears and blood flow at the conjunctiva and the episclera. The channels in the sclera will close after a short period of time.

Further, when the channels are closed, therapeutic agents such as macromolecules are trapped within the sclera, i.e. the macromolecules would not be easily washed out. The trapped macromolecules act as a depot (FIG. 7) enabling prolonged release at a higher dose to the neighboring choroidal and retinal tissues. Since the drug depot is at proximity, a higher flux of macromolecules can reach these intraocular tissues. In addition, the dose required for this method is lower than other methods as the diffusion distance is largely reduced. Thus, using the current invention, treatment for choroidal neovascularization can be improved. In addition, drugs may reach the retina and macular, especially when the retinal epithelium is leaky as in the case of macular degeneration. In addition, unlike iontophoresis, therapeutic agents such as the macromolecules need not to be charged, as the enhancement is due to the creation of channels instead of the electro-repulsion force in the case of iontophoresis. Advantageously, the present invention allows transscleral delivery of macromolecular agents to the target site in intrascleral space.

As is demonstrated in the Examples, the present invention utilizes the cavitation effect for the enhancement of intrascleral delivery of therapeutics. Preferably, the energy input of each ultrasound application in the present invention exceeds the threshold energy for generating cavitation bubbles (44). In an embodiment, the application of ultrasound at about 1 MHz and about 0.5 W/cm$^2$ creates cavitation bubbles having a radius of about 0.57 μm (45) and a microjet diameter, being about one tenth of the radius (46), of about 57 nm, which is an order of magnitude larger than the size of the FITC-BSA (3.6 nm (47)) exemplified herein. The size of the cavitation bubbles can be optimized by varying parameters such as, the frequency, power, waveform, wavelength, and duration of the ultrasound application.

System for Intrascleral Delivery of Therapeutic Agents

This invention provides a system for delivering therapeutic agents to a target site in intrascleral space using ultrasound. The system comprises: an ultrasound-generating device coupled with a well for transmitting and directing ultrasound to a desired site of the sclera. The ultrasound generated from the ultrasound-generating device creates cavitation, and thereby allowing the therapeutic agent to permeate across the desired site of the sclera to reach the target site in intrascleral space. In an embodiment, the ultrasound generating device is placed above the sclera at a distance of about 0.5 mm to about 5 mm. In another embodiment, the ultrasound is applied at a frequency of about 20 kHz to about 2.5 MHz. In another embodiment, the ultrasound is applied at a power of no greater than about 4 W/cm$^2$, preferably no greater than about 2 W/cm$^2$.

The term "ultrasound-generating device," as used herein, includes any apparatus capable of generating ultrasonic signals. In an embodiment, the ultrasound-generating device is an ultrasound applicator comprising: an electrical signal generator coupled with a power amplifier and an ultrasound transducer. Electrical signals are emitted from the signal generator, amplified by the amplifier, and converted into mechanical ultrasonic signals (vibrations) in the ultrasound transducer, whereby ultrasound is produced.

In an embodiment, the well comprises one or more ultrasound-transmitting media. Suitable ultrasound-transmitting media include, but are not limited to, substances such as air, fluids, aqueous solutions, water, and any combination thereof.

The ultrasound-generating device and the well can be placed in any position suitable for enhanced delivery of therapeutic agents to the posterior segment of the eye. In an embodiment, the ultrasound transducer is placed inside the well (FIG. 1). Alternatively, the ultrasound transducer can be positioned in close proximity above the well. In addition, the ultrasound-generating device can be positioned above or inside the well in a perpendicular or an angular position. For example, the ultrasound-generating device or parts thereof, such as an ultrasound transducer, can be positioned at an angle of about 5°, about 7°, about 10°, about 12°, about 15°, about 17°, about 20°, about 22°, about 25°, about 27°, or about 30° above the well.

Figure 2:
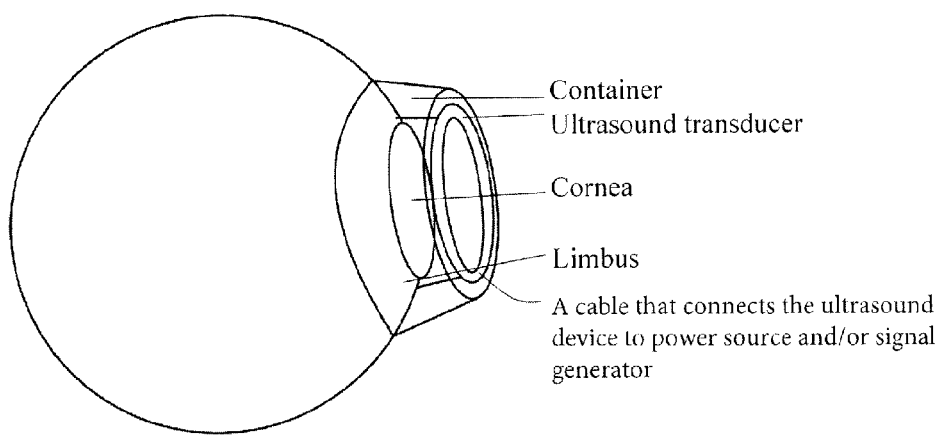
FIG. 2 is a schematic diagram illustrating the set up of an exemplified delivery system of the present invention. The ultrasound applicator is positioned around the limbus.
Figure 3:
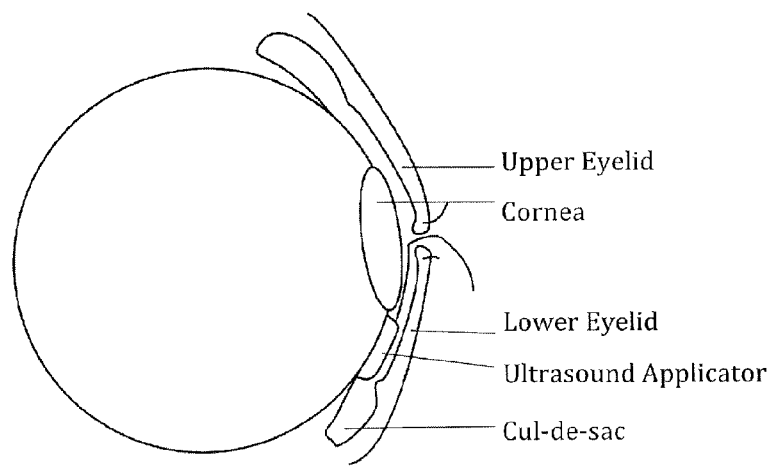
FIG. 3 is a schematic diagram illustrating the set up of an exemplified delivery system of the present invention. The ultrasound applicator is positioned in the cul-de-sac.
Figure 4:
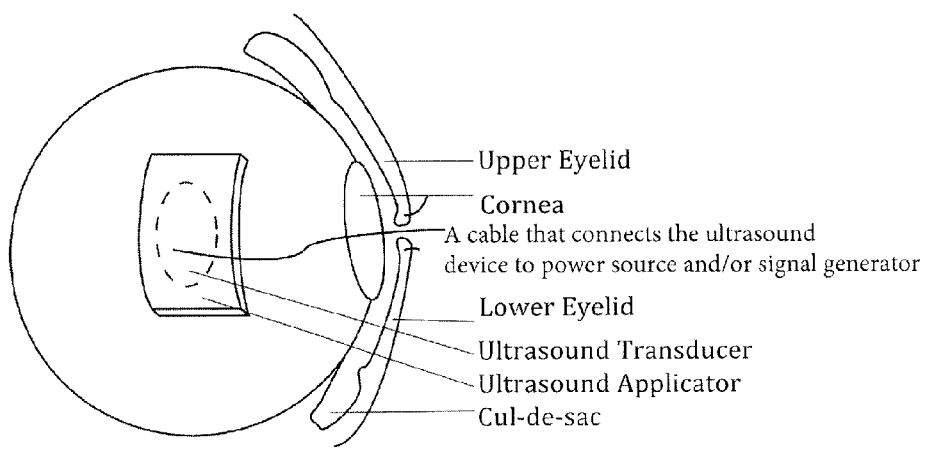
FIG. 4 is a schematic diagram illustrating the set up of an exemplified delivery system of the present invention. The ultrasound applicator is positioned in the posterior segment of the eye of a subject. Placing the applicator at the posterior segment is non-invasive and can be achieved, for example, by turning the eyeball of the subject.

Further, the ultrasound-generating device coupled with the well can be in any position relating to the eye, as long as ultrasound can be effectively directed to a desired site of a sclera allowing therapeutic agents to be delivered to a target site in intrascleral space. In an embodiment, the ultrasound-generating device is positioned above an exposed part of the sclera (FIG. 1). In a specific embodiment, the ultrasound-generating device is positioned around the limbus (FIG. 2). In another embodiment, the ultrasound-generating device is positioned in the cul-de-sac (FIG. 3). Additionally and alternatively, the ultrasound-generating device is positioned at the posterior segment of the eye (FIG. 4).

In addition, the ultrasound-generating device or the well can be positioned above or around the eye in a perpendicular or an angular position. For example, the ultrasound-generating device and/or the well can be positioned at an angle of about 5°, about 7°, about 10°, about 12°, about 15°, about 17°, about 20°, about 22°, about 25°, about 27°, or about 30° above or around the eye. In addition, the well may optionally contain one or more therapeutic agents, and may further comprise any device suitable for enhanced release and/or delivery of therapeutic agents to the target site in intrascleral space.

"Therapeutic agents," as used herein, include but are not limited to, any drugs, medicaments, antibodies, glycopeptides, dissolution compounds, genetic materials such as DNA and RNA, proteins or peptides, liposomes, lipids, synthetic or natural polymers or polymeric conjugates, macromolecules, nanocarrier or microcarrier encapsulated drug molecules, pharmaceutical formulations, any other substance capable of producing therapeutic actions, and any mixtures thereof. Further, the therapeutic agents can be combined with one or more pharmaceutically acceptable carriers, including but not limited to, a diluent, adjuvant, excipient, or vehicle with which the therapeutic agent is administered. In addition, the therapeutic agents can be formulated into, such as for example, a liquid solution, a gel, a spray, a particle, a granule, and a semi-liquid.

"Macromolecule" or "macromolecular agents," as used herein, refer to an agent having a molecular weight of higher than about 5000 Dalton, including but not limited to, proteins, polypeptides, polynucleotides, antibodies, glycopeptides/glycoproteins, liposomes, lipids, synthetic or natural polymers or polymeric conjugates, and nanocarrier or microcarrier encapsulated drug molecules. In addition, the well can be of any shape capable of cooperating with the ultrasound-generating device for transmitting ultrasonic signals and/or delivering therapeutic agents to the target site in intrascleral space. In an embodiment, the well is a hollow tube. In other embodiments, the well is in a shape of, such as for example, a cone, a sphere, a cylinder, a tetrahedron, or any irregular shape. In addition, the ultrasonic surface or geometric form of the well facing the sclera may be of many different shapes, such as for example, cylindrical, oval, elliptical, square, round, rectangular, and multi-angular shape.

Further, the present invention is convenient for clinicians to use in actual settings because the system does not require a standoff distance between the ultrasound-generating device and the sclera. Instead, the delivery system can be placed in close proximity or even in contact with the sclera. In an embodiment, an ultrasound transducer (the site of ultrasound generation) is positioned above the sclera at a distance of about 0.5 mm to about 5 mm in a well placing in contact with the sclera. In certain embodiments, the ultrasound-generating device, such as an ultrasound transducer, is positioned at a distance of about 0.6 mm to about 4.5 mm, about 0.7 mm to about 4.0 mm, about 0.8 mm to about 3.5 mm, about 0.9 mm to about 3.0 mm, about 1.0 mm to about 2.5 mm, about 1.1 mm to about 2.0 mm, about 1.2 mm to about 1.5 mm above the sclera.

Parameters of Ultrasound Application

The present invention allows effective delivery of macromolecular therapeutic agents by applying low-energy, low-frequency ultrasound for a short duration; thus, it is non-invasive and produces fewer side effects, as compared to the prior art techniques. Low energy ultrasound generates less heat, and thus, causes little damages to the sclera tissues. In addition, creation of temporary channels causes little damage to the scleral structure.

"Ultrasound," "ultrasonic signals," or "ultrasonic energy," as used herein, includes in addition to their ordinary meanings, mechanical energy transferred through longitudinal pressure or compression waves having a frequency greater than the upper limit of human audible range. Ultrasonic energy can be emitted as continuous or pulsating waves, depending on the parameters of a particular application. Additionally, the amplitude during each pulse can be constant or varied. Further, ultrasonic energy can be emitted in any suitable waveform, including but not limited to, sinusoidal waves, triangle waves, square waves, and any combination thereof.

The present invention applies ultrasound at a frequency of about 20 kHz to about 2.5 MHz. Thus, the ultrasound-generating device, such as a signal generator, is adapted to produce ultrasound signal at a frequency of about 20 kHz to about 2.5 MHz. The ultrasound frequency for each application can be constant or varied. In certain embodiments, the ultrasound signal is at a frequency of about 20 kHz to about 1 MHz, about 30 kHz to about 800 kHz, about 40 kHz to about 700 kHz, about 50 kHz to about 600 kHz, about 60 kHz to about 500 kHz, about 70 kHz to about 400 kHz, about 80 kHz to about 300 kHz, about 90 kHz to about 100 kHz. For adequate cavitation effect, any frequency exceeding 2.5 MHz is less desirable.

The diffusivity of therapeutic agents such as macromolecular agents can be optimized by lowering ultrasound frequency. In certain preferred embodiments, the ultrasound is applied at a frequency of about 20 kHz to about 500 KHz, about 20 kHz to about 400 kHz, about 20 kHz to about 300 kHz, about 20 kHz to about 200 kHz, about 20 kHz to about 100 kHz, about 20 kHz to about 90 kHz, about 20 kHz to about 80 kHz, about 20 kHz to about 70 kHz, about 20 kHz to 60 kHz, about 20 kHz to about 50 kHz, about 20 kHz to about 40 kHz, and about 20 kHz to about 30 kHz.

In addition, the present invention employs low-energy ultrasound, and thus avoids excessive heat generation which is harmful to ocular tissues. Thus, the ultrasound-generating device, such as the power amplifier, is adapted such that the ultrasonic signals emitted by the transducer have power no greater than about 4 W/cm$^2$. In certain embodiments, ultrasound has power no greater than about 3.5 W/cm$^2$, about 3 W/cm$^2$, or about 2.5 W/cm$^2$. Preferably, in order to minimize heat generation in ocular tissues, ultrasound has power no greater than about 2 W/cm$^2$, about 1 W/cm$^2$, about 0.5 W/cm$^2$, about 0.4 W/cm$^2$, about 0.3 W/cm$^2$, about 0.2 W/cm$^2$, or about 0.1 W/cm$^2$.

In addition, the present invention is capable of delivering therapeutic agents to the target site in intrascleral space by applying ultrasound for a short duration, such as, less than about 5 minutes. The time necessary for effective delivery of therapeutic agents also depends on various parameters, such as for example, the chemical and pharmaceutical characteristics of the agent, the molecular weight of the agent, the dosage, the site of delivery, the frequency, power, and waveform of the ultrasonic signals, the distance between the site of ultrasound generation and the target site in intrascleral space, the number of ultrasound applications in each treatment, and the ultrasound-transmitting medium.

In certain embodiments, the therapeutic agents can be effectively delivered to the target site by applying ultrasound for less than about 5 minutes, about 4 minutes, about 3 minutes, about 2 minutes, about 60 seconds, about 50 seconds, about 40 seconds, about 30 seconds, about 25 seconds, about 20 seconds, about 15 seconds, about 12 seconds, about 10 seconds, about 8 seconds, or about 5 seconds.

In the present invention, ultrasound can be applied as continuous or pulsating waves with duty cycle ranging from about 10% to about 90%. The amplitude of each wave may vary according to the ultrasound power. Further, repeated ultrasound treatments can be performed, while still allowing safe and effective delivery of therapeutics. For example, up to about 5, about 4, about 3, or about 2 ultrasound treatments can be performed for each delivery as desired.

In addition, for consecutive ultrasound treatments, ultrasound application can be performed with a period of lapse of at least about 1 minute, about 1.5 minutes, about 2 minutes, about 2.5 minutes, about 3 minutes, about 3.5 minutes, about 4 minutes, about 4.5 minutes, about 5 minutes, about 5.5 minutes, about 6 minutes, about 7 minutes, about 8 minutes, about 9 minutes, about 10 minutes, about 11 minutes, about 12 minutes, about 13 minutes, about 14 minutes, or about 15 minutes, without causing excessive heat or tissue damages to the eye.

In addition, after ultrasound application, therapeutic agents can be placed in contact with the target sclera tissue to enhance penetration of therapeutic agents into intrascleral space. The precise duration may vary, depending on parameters, such as for example, the desired therapeutic effects, the target site of delivery, the chemical and pharmaceutical characteristics of the agent, the molecular weight of the agent, the dosage, the frequency, power, and waveform of the ultrasonic signals, the number of and duration of ultrasound applications, and the desired depth of penetration. In certain embodiments, therapeutic agents are placed in contact with the sclera tissue for less than about 30 minutes, about 25 minutes, about 20 minutes, about 15 minutes, about 10 minutes, about 5 minutes, or about 3 minutes.

Further, therapeutics can be provided to a desired site of the sclera, prior to, during, or after ultrasound application. Since the enhancement of drug delivery occurs after but not during ultrasound application, therapeutics (such as in a form of hydrogel or solution) can be provided after ultrasound pretreatment. Using this ultrasound-pretreatment sequential regime, the small periocular space can be optimally utilized when the target location is the posterior segment of the eye.

The precise value of each parameter may vary, depending on the desired therapeutic effects, the target site of delivery, the chemical and pharmaceutical characteristics of the agent, the molecular weight of the agent, the dosage, the frequency, power, and waveform of the ultrasonic signals, the number of and duration of ultrasound applications, the desired depth of penetration, and the ultrasound-transmitting medium.

In addition, the pattern and the frequency of ultrasound can be altered by adjusting the ultrasound-generating device. For instance, by adjusting the amplifier, the power of the signal can be changed, causing the power of the ultrasound produced to change simultaneously. Since each ultrasound transducer has a specific workable range, a suitable one can be selected based on the particular operation parameters. Thus, the enhanced delivery of therapeutic agents to intrascleral space can be achieved using ultrasound signals with appropriate parameters as specified in the application.

Enhancement of Delivery of Macromolecular Therapeutics

The structure of sclera, though different from stratum corneum and fibrin clot, is amenable for disturbance by ultrasound. Sclera has only a sparse population of fibroblasts. The connective tissue is mainly a mesh composed of interlacing fiber bundles rich in collagen and elastin, surrounded by randomly oriented proteoglycan fibers (48, 49). The effective diffusivity of macromolecules through this fibrous structure is directly proportional to porosity and inversely proportional to tortuosity (35). It is possible that cavitation loosens the elastic fiber network and creates more open channels for protein transport. Ultrasound energy may also non-covalently modify the proteoglycan fiber morphology, similar to its effect on fibrin fibers and self-assembled peptide fibers (41, 50). Edwards and Prausnitz applied the fiber matrix theory to mathematically model the solute permeability through the sclera and predicted that a change in the proteoglycan architecture could reduce the diffusional resistance against macromolecules (37).

Figure 16A:
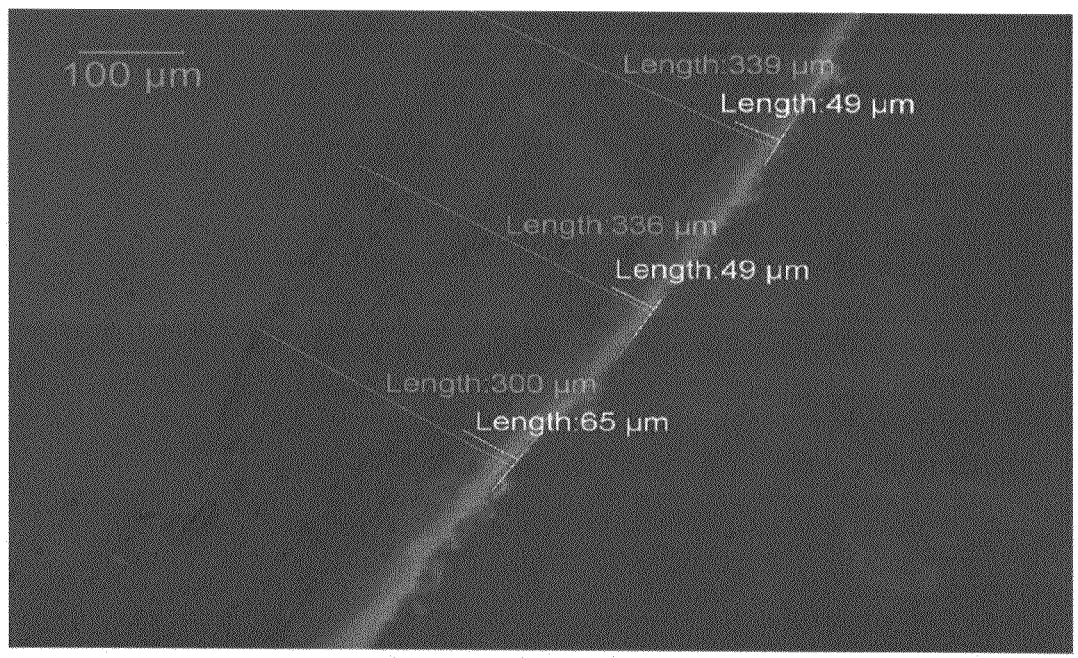
FIG. 16 shows the effect of time lapse on ultrasound enhancement. Representative cryosections show the penetration of fluorescent green colored FITC-BSA into the rabbit sclera when: a) the eye was immersed in FITC-BSA solution without prior ultrasound treatment (control); b) the eye was treated in ultrasound while in BSS+® buffer, remained being immersed in the colorless buffer for 15 minutes and then transferred to FITC-BSA solution for another 15 minutes. S: sclera; O: orbital side; U: uveal side. The mean and standard deviation are shown in (c), averaging from over 60 measurements and 3 eyes for each condition. No statistical significance was found between the two groups (p=0.34)
Figure 16B:
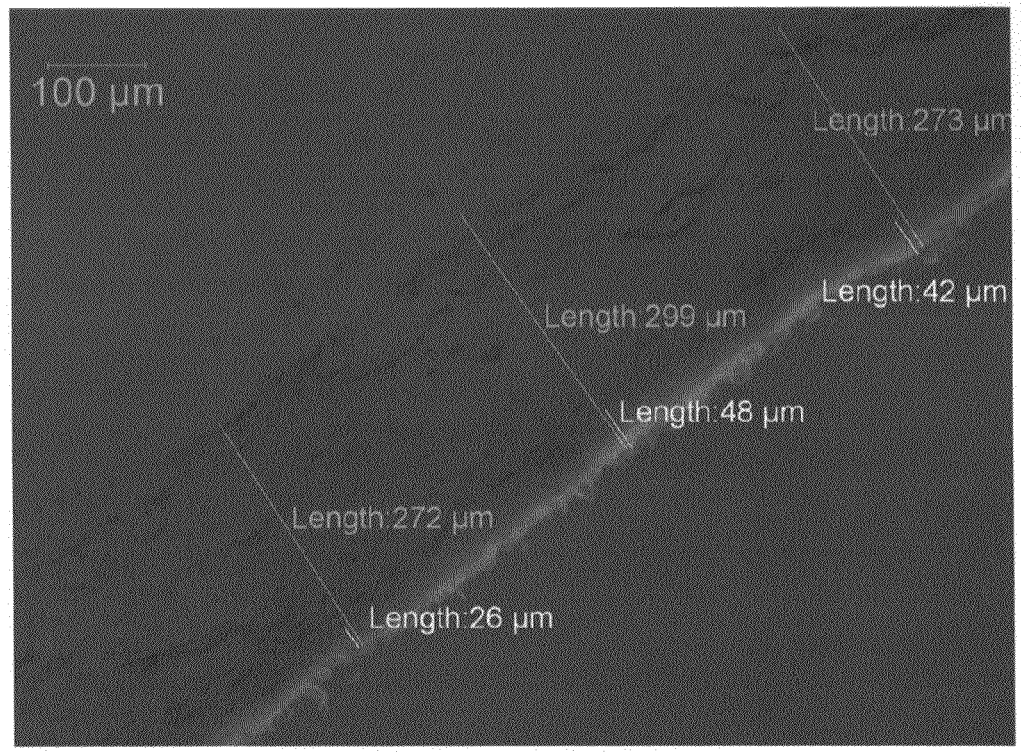
Figure 16C:
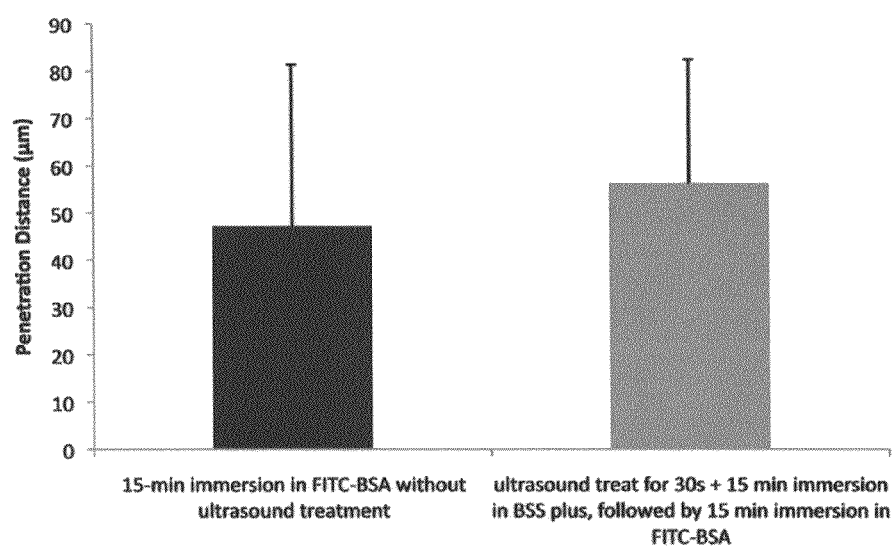
Figure 18:
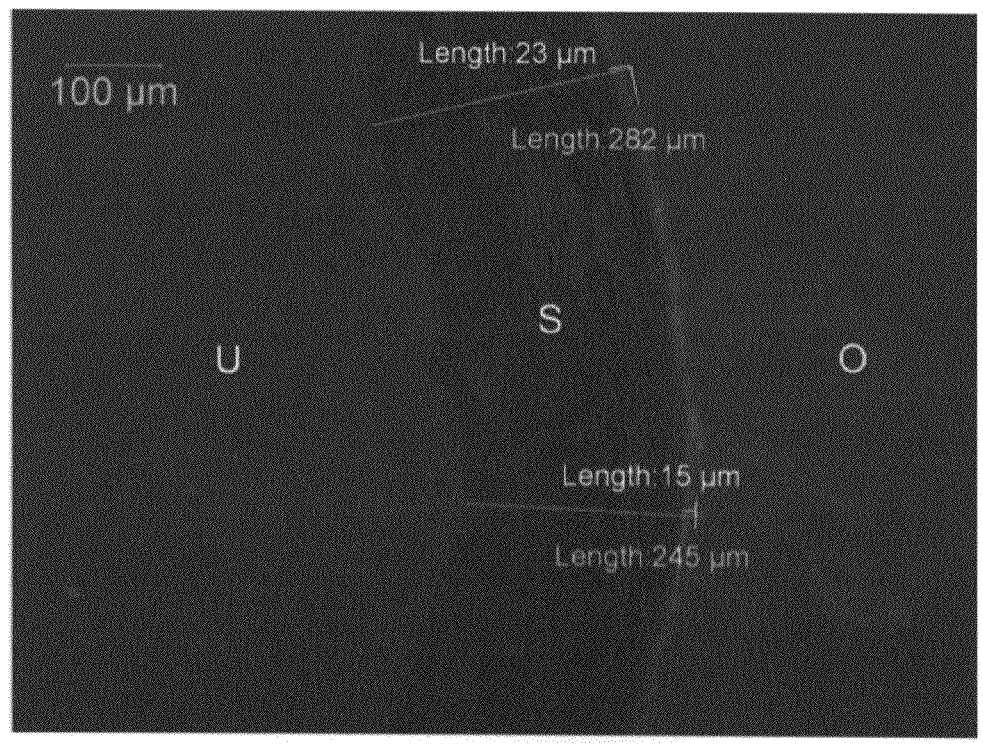
FIG. 18 shows intrascleral protein penetration in the absence of diffusion time after ultrasound application. A representative cryosection taken from a data set of over 60 measurements from 3 eyes is shown. S: sclera; O: orbital side; U: uveal side.
Figure 19:
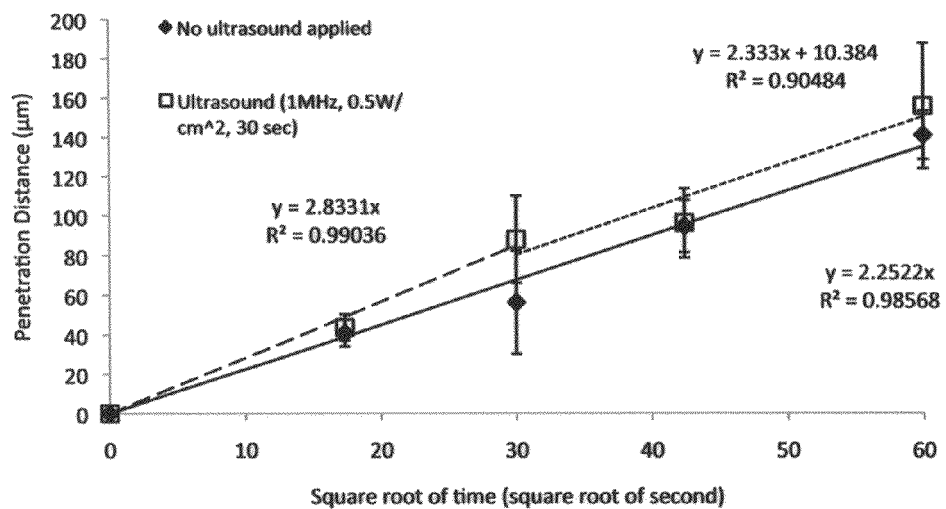
FIG. 19 illustrates calculation of intrascleral diffusivity of FITC-BSA. The values were deduced from slopes in the graphs plotting penetration distance against the square root of time. The diffusivity at 37° C. with ultrasound treatment was found to be $6.17 \times 10^{-08}$ cm$^2$/sec in the first 15 min and $4.18 \times 10^{-8}$ cm$^2$/sec from 15 to 60 min. The diffusivity in the control (without ultrasound application) was $3.90 \times 10^{-08}$ cm$^2$/sec.

The present invention provides an enhanced delivery of therapeutic agents to intrascleral space by applying ultrasound according to various parameters specified in the subject application. As exemplified in the Examples, the application of short duration (30 s), medium-frequency (1 MHz) ultrasound at low power (0.5 W/cm$^2$) imposes physical modulation to the barrier property of the rabbit sclera, resulting in a significant increase in the depth of penetration by FITC-BSA (FIG. 16). In a specific embodiment, FITC-BSA, a 65 kDa protein measuring 3.62 nm in hydrodynamic radius, was employed as a model macromolecular drug. Experiments revealed that the ultrasound-induced convective flow is not the dominant mechanism for ultrasound-enhanced intrascleral delivery, since penetration immediately after ultrasound treatment is limited (FIG. 18). Instead, enhanced diffusion is observed after ultrasound application (FIG. 16 and FIG. 19).

Advantageously, the present invention enhances protein delivery by applying low-energy, low-frequency ultrasound, and thus avoids excessive heat generation which is harmful to ocular tissues. Due to the low energy input, the temperature rise on the scleral surface is less than about 1° C. As exemplified in the Examples, less than about 0.5° C. temperature rise is observed on the scleral surface. According to the Stokes-Einstein equation, diffusivity increases proportionally with absolute temperature. Thus, this minor temperature increase cannot account for the increase in diffusivity (FIG. 19). Rather, an enhanced intrascleral delivery is largely due to the cavitation effect, a nonthermal phenomenon of ultrasound.

The present invention can significantly increase the diffusivity of macromolecular agents. More surprisingly, the diffusivity of macromolecules can be further optimized by lowering the ultrasound frequency. The Experiments detailed below demonstrate that the present invention utilizes the cavitation effect as the dominant mechanism for enhanced intrascleral delivery. As the efficiency of cavitation is inversely proportional to ultrasound frequency (51), the intrascleral flux of protein can be further increased by decreasing the ultrasound frequency to the low frequency regime, such as about 20-100 kHz. To illustrate, only a 1.6-fold increase in diffusivity is observed when ultrasound is applied at a medium frequency of about 1 MHz. In comparison, a significant increase in diffusivity can be achieved by applying ultrasound at a lower frequency range, such as about 20-100 kHz.

More advantageously, the present invention applies ultrasound at a low energy level to limit the temperature rise, and thereby eliminating safety concerns caused by excessive heating of ocular tissues (52). For diagnostic applications using ultrasound, common medical safety regulations only permit a maximal increase of about 1° C. in ocular tissues. The observed temperature increase in the present invention is well below this cutoff.

Figure 20A:
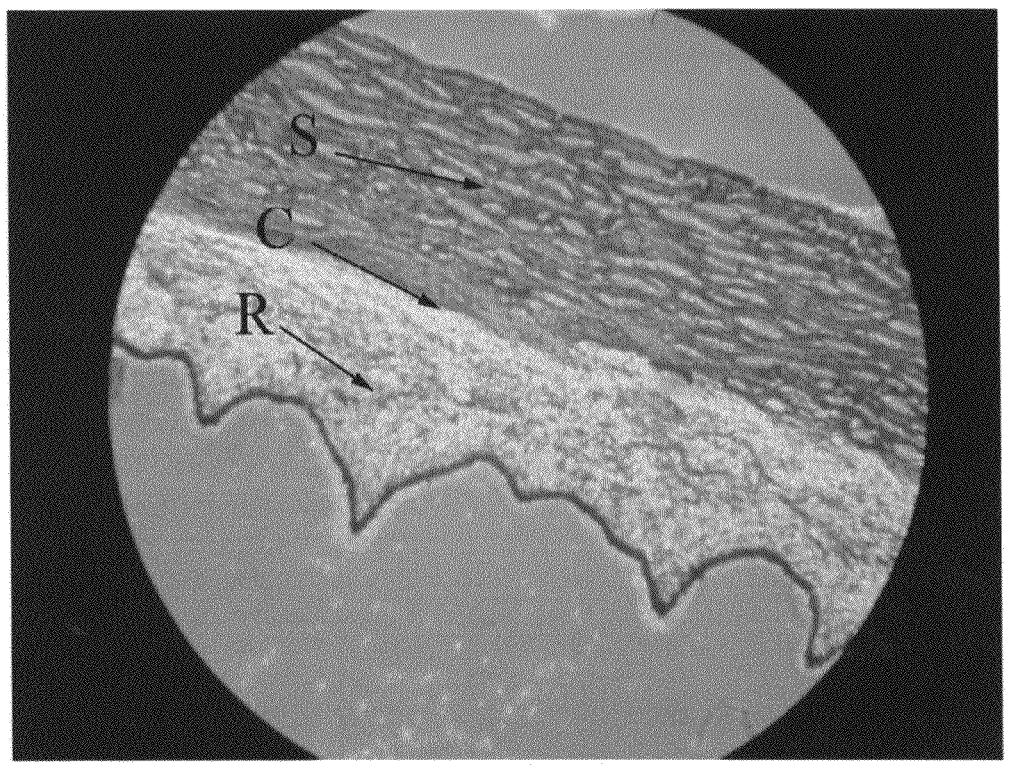
FIG. 20 shows histological assessment of the effect of ultrasound on ocular structures. Tissue sections were prepared with hematoxylin and eosin (H&E) stain: a) from a control eye without ultrasound treatment; b) from a rabbit eye exposed to a 30 s pulse of ultrasound at 1 MHz and 0.5 W/cm$^2$. S: sclera; C: choroid; R: retina.
Figure 20B:
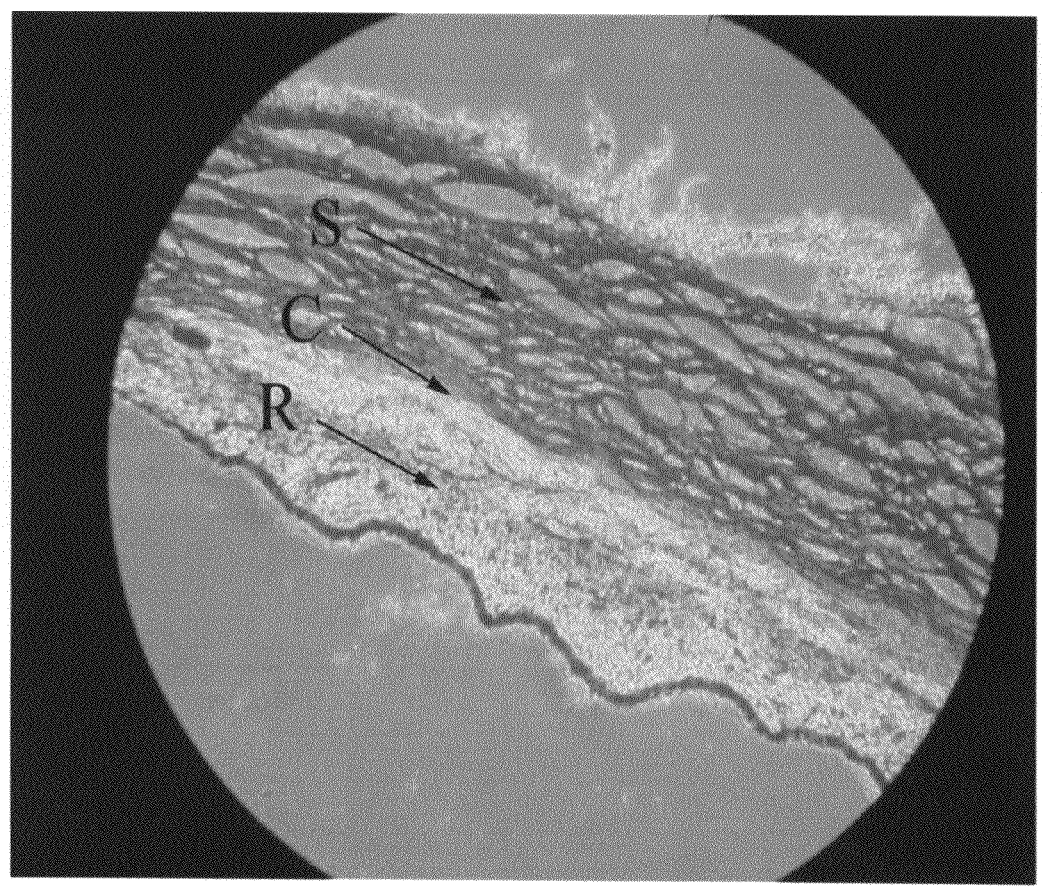

Furthermore, the present invention will not cause substantial harm to the ocular structure and tissues. As demonstrated in the Examples, histological examination after ultrasound application according to the present invention revealed that the present invention does not compromise the structure of the scleral and retinal tissues (FIG. 20). The morphological appearance of the eye, especially of the retinal layer, did not show any apparent abnormality as compared to the normal untreated control. The low-intensity ultrasound exposure did not cause any adverse effect of the retina or its detachment.

Figure 17A:
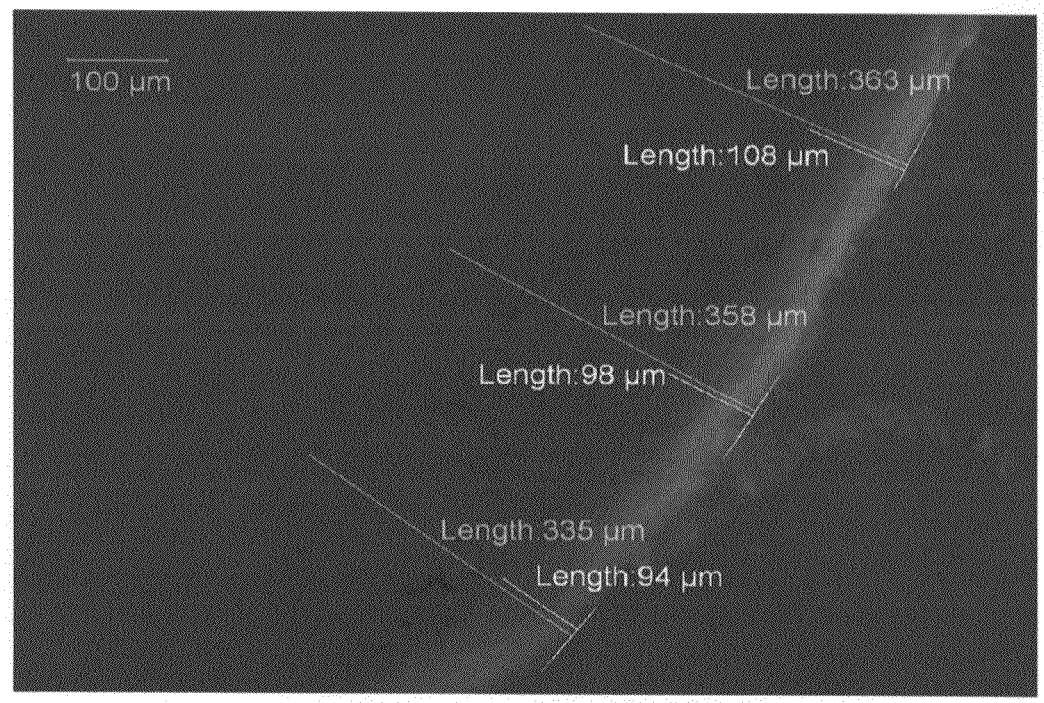
FIG. 17 shows reproducibility of ultrasound-enhanced protein transport. Representative cryosections show the extent of FITC-BSA penetration into the rabbit sclera: a) at 15 minutes after the first ultrasound application; b) at 15 minutes after the second ultrasound application. There was 15-minute waiting time between the first and second ultrasound. S: sclera; O: orbital side; U: uveal side. The mean and standard deviation are shown in (c), averaging from over 40 measurements from at least 2 eyes for each condition. No statistical significance was found between the two groups (p=0.21)
Figure 17B:
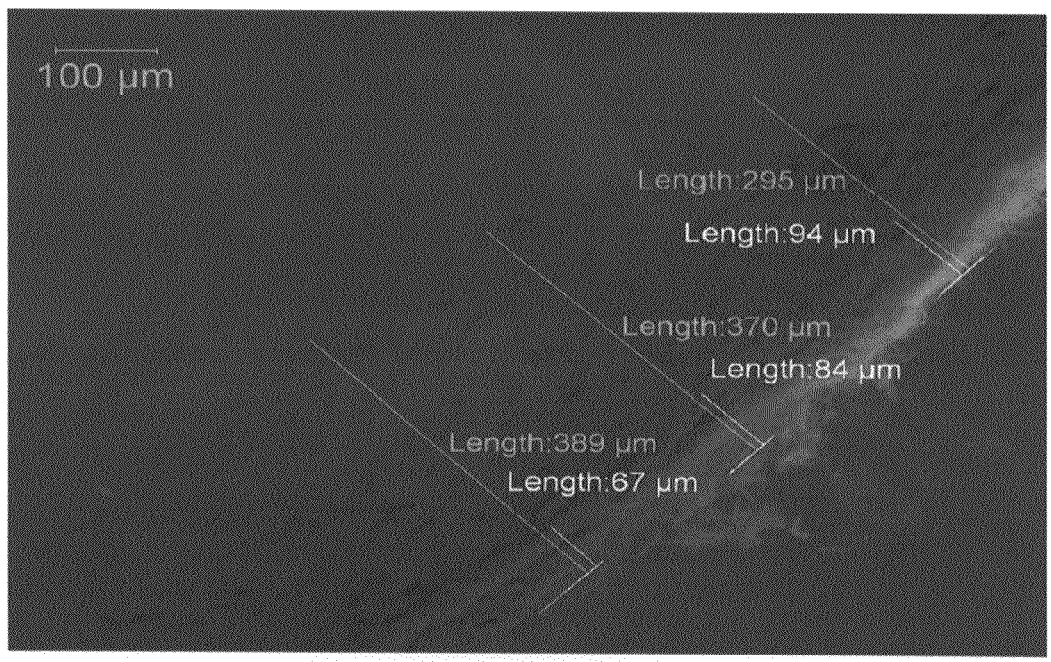
Figure 17C:
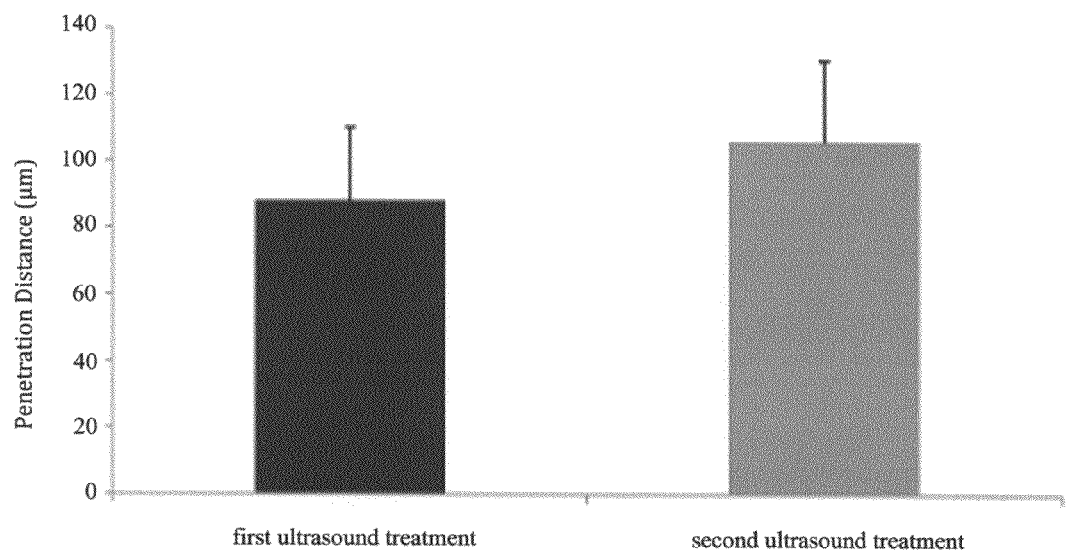

Still further, because the increase in scleral permeability by ultrasound according to the present invention is repeatable, repeated ultrasound applications can be performed to optimize the delivery effects. The acellular and fibrous nature of the sclera permits the restoration of the barrier function shortly after ultrasound treatment. As demonstrated in the Examples, ultrasound application creates a temporary window of about 15 minutes during which the intrascleral diffusivity was enhanced (FIGS. 16 and 19). After 15 minutes, the diffusivity decreased to a value comparable to the control, suggesting the fading of ultrasound effects. When ultrasound was re-applied, similar augmentation of protein penetration was observed (FIG. 17). This observation is because that the transport is enhanced by the ultrasound's physical disturbance of the fiber structures rather than a permanent damage to living cells. Upon termination of ultrasound application, un-stretching of elastic fibers and resuming of the original pore structure can be achieved. Re-assembly of disaggregated fibers, driven by thermodynamics, will take place after the ultrasound treatment ends. Another cycle of fiber restructuring is initiated when ultrasound is reapplied, allowing repeated delivery. Further, after therapeutic molecules are delivered, the ability for the scleral barrier to reseal is critical for eye protection. As is demonstrated in the Examples, scleral barrier is resealed after ultrasound application of the present invention.

In addition, the new method is safe and non-invasive when compared to the periocular and intravitreal injection, and scleral/intrascleral implants. In ocular applications, ultrasound has been widely used for diagnostic purposes like measuring intraocular pressure without causing eye damage. As is shown in examples described below, channels created by ultrasound would close at 15 minutes after a 30-second ultrasound application. Also, the present invention does not require invasive procedures like surgery or injection through the eye tissue.

Further, the present invention is more user-friendly compared with the periocular and intravitreal injection and scleral/intrascleral. Firstly, the medical skills required for performing this invention need not be as high as periocular or intravitreal injection. The ultrasound applicator is applied to the eyeable part of the sclera, which eliminates the side effects in periocular injection. Secondly, the time of ultrasound applied is relative short, e.g. 30 seconds, which can be easily accepted by patients.

Thus, the present invention provides a safe and effective system and method for delivering therapeutics, particularly macromolecules such as proteins and nucleic acids, into a target site in intrascleral space. Therapeutic agents such as macromolecules can be delivered to intrascleral space at a depth of at least about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 230 µm, about 250 µm, about 280 µm, or about 300 µm.

The maximum depth of penetration may vary, depending on for example, the chemical and pharmaceutical characteristics of the agent, the molecular weight of the agent, the dosage, the frequency, power, and waveform of the ultrasonic signals, and the number of and duration of ultrasound applications. In an embodiment, fluorescent albumin, a 65 kDalton macromolecule, was effectively delivered to an intrascleral site of about 110 µm by applying low-power (0.5 W/cm$^2$), medium-frequency (1 MHz) ultrasound for a short duration (30 seconds).

The depth of penetration can be further optimized by adjusting various parameters according to the subject application, such as for example, by lowering the ultrasound frequency to about 20 kHz-100 kHz, increasing ultrasound intensity, increasing the number and duration of ultrasound applications. By optimizing various parameters, therapeutics can be delivered to intrascleral space at a depth of up to about 0.1 mm, about 0.2 mm, about 0.3 mm, about 0.4 mm, about 0.5 mm, about 0.6 mm, about 0.7 mm, about 0.8 mm, about 0.9 mm, or about 1.0 mm.

In addition, in actual clinical settings, therapeutics can be delivered to intrascleral space at a depth of up to about 100% of the full scleral thickness, about 90% of the full scleral thickness, about 80% of the full scleral thickness, about 70% of the full scleral thickness, about 60% of the full scleral thickness, about 50% of the full scleral thickness, about 45% of the full scleral thickness, about 40% of the full scleral thickness, about 35% of the full scleral thickness, about 30% of the full scleral thickness, about 25% of the full scleral thickness, about 20% of the full scleral thickness, about 15% of the full scleral thickness, about 10% of the full scleral thickness, or about 5% of the full scleral thickness.

In addition, the present invention can create localized cavitation effect on sclera tissues. Thus, therapeutic agents can be directed to the target site in intrascleral space. The intrascleral position means that the therapeutics can be in proximity to the following intraocular tissue: the anterior hyaloid membrane and all of the optical structures behind it, such as for example, the vitreous humor, retina, choroid, optic nerves, and any combination thereof.

Advantageously, the present invention is capable of producing temporary channels (cavitation bubbles) in ocular tissues at a radius of up to about 0.1 µm, about 0.2 µm, about 0.3 µm, about 0.4 µm, about 0.5 µm, about 0.6 µm, about 0.7 µm, about 0.8 µm, or about 0.9 µm. In addition, the microjet diameter can be up to about 10 nm, about 20 nm, about 30 nm, about 40 nm, about 50 nm, about 60 nm, about 70 nm, about 80 nm, or about 90 nm.

The radius of the temporary channels and the microject diameter can be further optimized by adjusting various parameters according to the subject application, such as for example, the frequency, power, waveform, and the pulse of the ultrasound, and the duration of application, for achieving the desired treatment effect. In an embodiment, low-power (0.5 W/cm$^2$), medium-frequency (1 MHz) ultrasound is applied for a short duration of 30 seconds, and generates temporary channels in ocular tissues at a radius of up to about 0.57 µm and the microject diameter up to about 57 nm.

The creation of temporary channels enhances ocular diffusivity of therapeutic agents. In an embodiment, ocular diffusivity of therapeutic agents is increased up to about 2 folds due to ultrasound application. In certain embodiments, ocular diffusivity of therapeutic agents is increased up to about 20 folds, about 17 folds, about 15 folds, about 12 folds, about 10 folds, about 8 folds, about 7 folds, about 6 folds, about 5 folds, about 4 folds, about 3 folds, or about 2 folds due to ultrasound application.

In other embodiments, ocular diffusivity is increased to about $9.0\times10^{-8}$ cm$^2$/sec, about $8.0\times10^{-8}$ cm$^2$/sec, about $7.0\times10^{-8}$ cm$^2$/see, about $5.0\times10^{-8}$ cm$^2$/see, about $4.0\times10^{-8}$ cm$^2$/sec, or about $3.0\times10^{-8}$ cm$^2$/sec. In other embodiments, ocular diffusivity is increased to about $8.0\times10^{-7}$ cm$^2$/sec, about $7.0\times10^{-7}$ cm$^2$/see, about $6.0\times10^{-7}$ cm$^2$/sec, about $5.0\times10^{-7}$ cm$^2$/sec, about $4.0\times10^{-87}$ cm$^2$/sec, about $3.0\times10^{-7}$ cm$^2$/sec, about $2.0\times10^{-7}$ cm$^2$/sec, or about $1.0\times10^{-7}$ cm$^2$/sec.

The increase in diffusivity can be varied, depending on for example, the desired treatment effect, the chemical and pharmaceutical characteristics of the agent, the molecular weight of the agent, the dosage, the frequency, power, and waveform of the ultrasonic signals, the number of and duration of ultrasound applications, and the desired depth of penetration. In an embodiment, application of low-power (0.5 W/cm$^2$), medium-frequency (1 MHz) ultrasound for a short duration of 30 seconds increased ocular diffusivity of fluorescent albumin in 2 folds.

Advantageously, the present invention is capable of delivering therapeutic agents of high molecular weight into the target site in intrascleral space. Specifically, this invention provides an advantageous delivery method for macromolecular therapeutic agents, such as for example, PEGylated-aptamers (Macugen®), antibody fragments (Lucentis®), antibody (Avastin®), growth factors, and neurotrophic factors (e.g. ciliary neurotrophic factor (CNTF)).

In a specifically exemplified embodiment, the present invention is capable of intrascleral delivery of fluorescent albumin, a molecule having a molecular weight of about 65k Dalton. In other embodiments, therapeutic agents having a molecular weight of as much as about 150k Dalton, about 140k Dalton, about 130k Dalton, about 120k Dalton, about 110k Dalton, about 100k Dalton, about 90k Dalton, 80k Dalton, about 70k Dalton, about 60k Dalton, about 50k Dalton, about 40k Dalton, about 30k Dalton, about 20k Dalton, about 10k Dalton, about 5k Dalton, can be effectively delivered to the intrascleral space.

Further, therapeutic agents can be delivered via a microcarrier or nanocarrier. Certain types of microcarriers, such as microbubbles, can enhance the effect of cavitation and thus are useful for optimizing the delivery of therapeutic agents such as compounds, proteins, and gene products. Delivery via microcarriers or nanocarriers also protects therapeutic molecules from degradation, extends their release, and provides improved targeting functions. In certain embodiments, microcarriers include, for example, microbubbles and microparticles that enhance the cavitation effect and are useful for drug and gene delivery. Other embodiments include nanocarriers such as, for example, liposomes, polymeric micelles, polymeric vesicles, polymeric particles, protein particles, and peptide nanoparticles. In a specific embodiment, the nanocarrier is a liposome, having a lipid-containing wall defining an internal volume. Examples of formulations of liposomes and other microcarriers or nanocarriers are described in Stover T et al., J Pharmacol Exp Ther., 2003, 307:468-475; and Stover T C, et al., Clin Cancer Res., 2005, 11:3465-3474.

In an embodiment, microcarriers or nanocarriers used in the present invention typically have a radius or particle size of about 0.1 nm to about 0.9 µm. In certain embodiments, microcarriers or nanocarriers have a particle size such as a radius of about 0.1 nm to about 0.8 µm, about 0.2 nm to about 0.7 µm, about 0.3 nm to about 0.6 µm, about 0.4 nm to about 0.5 µm, about 0.5 nm to about 0.4 µm, about 0.6 nm to about 0.3 µm, about 0.7 nm to about 0.2 µm, or about 0.8 nm to about 0.1 µm. In certain embodiments, nanocarriers have a particle size such as a radius of about 0.1 nm to about 0.9 nm, about 0.2 nm to about 0.8 nm, about 0.3 nm to about 0.7 nm, or about 0.4 nm to about 0.6 nm. In certain embodiments, microcarriers have a particle size such as a radius of about 0.1 µm to about 0.9 µm, about 0.2 µm to about 0.8 µm, about 0.3 µm to about 0.7 µm, or about 0.4 µm to about 0.6 µm.

Additional nanocarriers include, but are not limited to, nanospheres, nanodendrimers, nanocolloids, nanodots, nanocolumns, and any combination thereof. Further description of nanocarriers such as liposomes and methods relating to their preparation and use may be found in Liposomes: A Practical Approach (The Practical Approach Series, 264), V. P. Torchilin and V. Weissig (Eds.), Oxford University Press; 2nd ed., 2003. Further description of nanocarriers may be found in S. M. Moghimi et al., Nanomedicine: current status and future prospects, FASEB J. 2005, 19, 311-30.

Advantageously, the present invention generates negligible heat in ocular tissues, and thus, avoids damages to ocular tissues and the structure of the eye. The temperature increase in ocular tissues is less than about 1° C., preferably less than about 0.9° C., preferably less than about 0.8° C., preferably less than about 0.7° C., preferably less than about 0.6° C., preferably less than about 0.5° C., preferably less than about 0.4° C., preferably less than about 0.3° C., preferably less than about 0.2° C., preferably less than about 0.1° C., more preferably less than about 0.05° C., and most preferably less than about 0.01° C.

Thus, the present invention allows safe, non-invasive and effective delivery of drugs at therapeutic levels to ocular tissues, useful for treating, alleviating, or ameliorating an eye disease, disorder, injury, inflammation, symptom, or condition, including but not limited to, choroidal neovascularization, age-related macular degeneration, diabetic retinopathy, glaucoma, retinitis pigmentosa, macular edema, macular degeneration, multirecurrent ptergyia, ocular toxoplasmosis, proliferative vitreoretinopathy (PVR), Stevens-Johnson syndrome (SJS), ocular cicatricial pemphigoid (OIP), an ocular degenerative condition, a post-surgery condition, ocular tissue injuries, ocular tumor, and any combination thereof.

The present invention is also useful for delivering therapeutics for useful for treating, alleviating, or ameliorating an eye disease, disorder, injury, inflammation, symptom, or condition, including but not limited to, anterior, intermediate, and posterior segment eye diseases, such as for example, chronic glaucoma, retinal detachment, sickle cell retinopathy, retinal neovascularization, subretinal neovascularization; rubeosis irides, choroiditis, posterior uveitis, neoplasms, retinoblastoma, pseudoglioma, neovascular glaucoma; neovascularization resulting following a combined vitrectomy and lensectomy, vascular diseases, retinal ischemic, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streaks, retinal artery occlusion, and neovascularization due to ocular injury.

The present invention provides, for the first time, a safe, effective, and feasible use of ultrasound for delivering macromolecular therapeutics such as therapeutic proteins into the sclera. Further, the weakening of the scleral barrier is not permanent nor is there any observable damage to the retinal tissue. For example, the present invention provides, in addition to microneedles and iontophoresis, an alternative and superior non-invasive drug delivery method by placing drugs close to the Bruch's membrane-choroid where neovascularization occurs in sight-threatening diseases (e.g. wet age-related macular degeneration). The depot effect further prevents drugs from being washed away by ocular fluid flow or episcleral blood flow, and thereby increasing the concentration gradient to drive the inward transport into the retina. In addition, the present invention can be used in combination with conventional drug delivery methods, such as for example, the intravitreal route, the systemic route, the transcorneal route, the periocular route, and the transscleral route, for achieving optimal therapeutic effects.

To our best knowledge, no work has been documented demonstrating the safe and effective use of ultrasound to enhance the delivery of macromolecular drugs via the transscleral route. There has been limited research on the use of ultrasound for ocular drug delivery. Ultrasound-mediated transcorneal delivery was reported to improve the transport of a low molecular weight compound (sodium fluorescein) through the cornea (Zderic et al. 2002 and Zderic et al. 2004). However, the transcorneal route is a longer and more difficult path to reach the posterior segment of the eye compared to the transscleral route in the present invention.

Further, the prior art techniques only demonstrated the delivery of low molecular weight compounds using ultrasound; in comparison, the present invention is capable of delivering macromolecular compounds and/or via microcarriers or nano drug carriers. Macromolecular compounds represent emerging therapeutics for serious eye diseases, while delivery via microcarriers or nanocarriers further protects drug molecules from degradation, extends their release, and provides improved targeting functions.

Although U.S. Published Patent Application No. 2008/0177220 suggests a conceptual idea of an ultrasound-mediated transscleral ocular delivery method, the reference does not teach delivery of therapeutics of high molecular weight or via microcarriers or nanocarriers. Rather, the reference only demonstrates transscleral delivery of sodium fluorescein, a low molecular weight compound.

Figure 7:
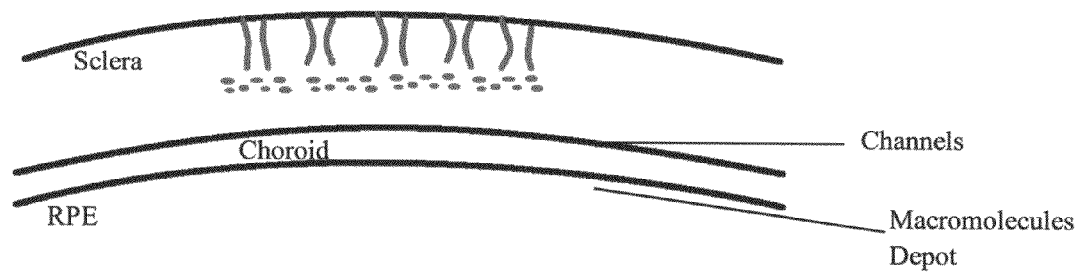
FIG. 7 is a schematic diagram showing the channels created by low frequency ultrasound and the macromolecules depot inside the sclera.

In addition, the reference teaches delivery of therapeutics across the sclera, choroid, and retinal pigmented epithelium into the vitreous. This transscleral delivery path by crossing sclera and two additional ocular tissues is, however, less efficient, as compared to that of the present invention, where therapeutics are delivered directly into the intrascleral space (FIG. 7). Drug delivery into the intrascleral space increases drug concentration in the inner sclera, which increases the flux into the intraocular tissue due to a steeper concentration gradient. In addition, the present invention creates the depot effect, allowing delivery of drugs to choroid, which is adjacent to the sclera. Further, the drug delivery method in U.S. Published Patent Application No. 2008/0177220 requires a continuous ultrasound application for about 10 minutes at 20 watts.

The high-intensity, long-duration ultrasound treatment is likely to cause excessive heating and irreversible damages to ocular tissues, and thus, presents substantial safety concerns for actual clinical use. Advantageously, the present invention achieves safe and effective delivery of macromolecules by applying ultrasound for a much shorter duration and at a lower intensity. Also, the drug delivery method in U.S. Published Patent Application No. 2008/0177220 requires a stand-off distance of 0.5 and 1.5 cm between the scleral surface and the ultrasound device, indicating that it would be invasive for placing the probe at the posterior segment of the eye. In addition, a standoff distance is less user-friendly in actual clinical settings. Advantageously, the present invention does not require any standoff distance. Instead, the ultrasound-generating device can be positioned above on the eye, while still allowing non-invasive or minimally invasive clinical applications.

Materials and Methods
Materials

FITC-BSA of molecular weight 65 kDa was obtained from Sigma (St. Louis, Mo.). Balanced Salt Solution Plus® (BSS+®) was purchased from Alcon (Fort Worth, Tex.), 0.1% FITC-BSA was prepared by dissolving FITC-BSA in BSS+®. All other chemicals were of analytical grade and purchased from Sigma (St. Louis, Mo.). All samples were light protected until fluorescence measurement.

Ex Vivo Experiment

Figure 6:
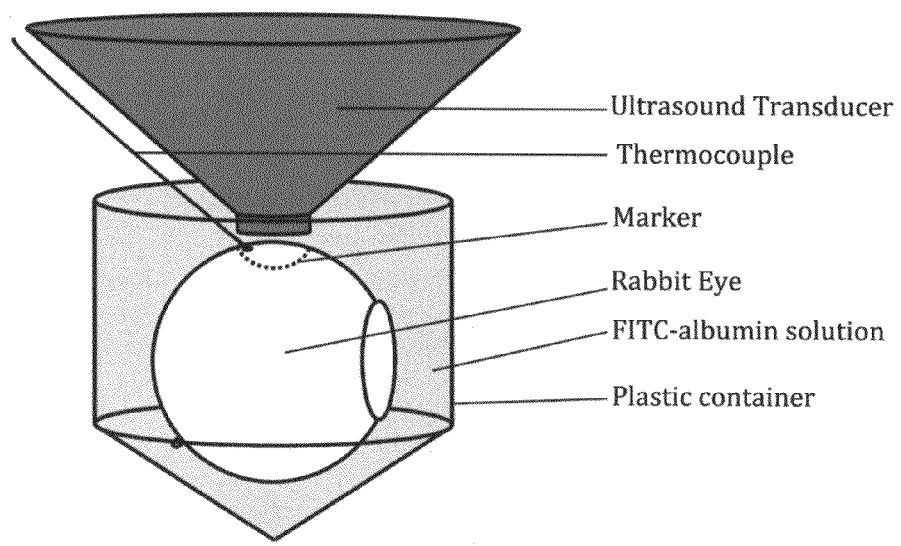
FIG. 6 is a schematic diagram illustrating the set up of in vitro experiments. The eye from a New Zealand White Rabbit is immersed in 4 ml of 0.1% FITC-albumin in BSS+®. The region of ultrasound application is labeled with a marker. The ultrasound probe is placed directly above the sclera near the equator and is in contact with the FITC-albumin solution. The scleral surface temperature before and after ultrasound application is measured by a thermocouple.

The eyes of New Zealand White Rabbits (6-month to one-year-old) were enucleated immediately after the rabbits were sacrificed. The eyes were kept on ice prior to experiments and the time lag never exceeded 15 minutes to ensure tissue freshness. All the periocular tissues (muscles and conjunctiva) were removed and the optic nerve was sealed with Vaseline®. The experimental set-up is schematically shown in FIG. 6. The eye was immersed in a container filled with 4 ml of 0.1% FITC-BSA or BBS+®. An ultrasound transducer with a probe size of 1 cm$^2$ (BTL-4000, BTL Industries, Inc., Clark, N.J.) was positioned a few millimeters above the sclera near the equator. The zone of ultrasound application was labeled with a marker. Ultrasound at a therapeutic frequency (1 MHz) and a low power input (0.5 W/cm$^2$) was applied for 30 seconds. The eye continued to be immersed in 0.1% FITC-BSA or BBS+® for different time intervals (5, 15, 30 and 60 minutes for 0.1% FITC-BSA; 15 minutes for BSS+®). All of the experiments were carried out at room temperature. The scleral surface temperature at the ultrasound application zone before and after treatment was measured using a thermocouple. Controls were performed by immersing the eyes for different time intervals without ultrasound application.

Cryo-Sectioning

Immediately after the ex vivo experiments, the whole eye was washed and immersed in a mould filled with optimum cutting temperature medium (O.C.T) (Leica, Wetzlar, Germany), followed by quick-freezing in liquid nitrogen. 10 μm thick sections across the marked ultrasound application zone of the eye were cut using a cryostat (CM1850, Leica, Wetzlar, Germany). Polylysine-coated slides were used for collecting the tissue sections.

Measurement of Protein Penetration

All images were acquired using a fluorescence microscope (BX 41, Olympus, Center Valley, Pa.). The image of the sclera was captured under optical mode, and FITC-BSA penetration into the sclera was captured under fluorescence mode (band-pass filter: 510-550 nm, dichroic mirror: 570 nm, barrier filter: 590 nm, exposure time: 100 ins). The pictures shown in the FIGS. 15-17 were merged images of these two modes. The thickness of the sclera and the penetration distance of FITC-BSA were obtained using the software SPOT® (Diagnostic Instruments, Inc., MI, USA). For each experiment or control, 2 to 4 eyes from different rabbits were used. Three tissue sections were obtained from each eye and at least 20 measurements on the penetration distance were made in each eye. Only images showing intact sclera were used for measurement to avoid ambiguity.

Calculation of Diffusivity

The one-dimensional diffusion model describing the penetration distance (L), diffusivity (D) and time of diffusion (t) is given by the equation below (23):

$$L = \sqrt{2Dt}. \quad (1)$$

A plot of the penetration distance versus the square root of time yields a straight line. The diffusivity is calculated from the slope, which equals $\sqrt{2}$ D.

The diffusivity measured at room temperature is converted to the value at 37° C. according to Stokes-Einstein equation, which gives $$\frac{D_{37}}{D_{20}} = \frac{310K \times \eta_{20}}{293K \times \eta_{37}}; \quad (2)$$

where D and η are diffusivity and viscosity respectively, with the temperature designated at the subscript. Since the experiment was conducted in dilute buffer solution, the viscosity of water is used.

Histological Study

The eye was immersed in BSS+® and ultrasound was applied as described above. To preserve the ocular tissues, 100 μl of 4% paraformaldehyde was injected into the retina via the optic nerve and the eye was then immersed in 4% paraformaldehyde for 1 day. After fixation, the eye was halved by a sharp razor. The eye was then cryoprotected by immersing in 30% sucrose overnight. After cryoprotection, O.C.T was added to displace the viterous inside the half eyecup. The half eyecup was embedded in O.C.T and was frozen in liquid nitrogen for sectioning. H&E stain was used to visualize the tissues.

Statistical Analysis

Data were analyzed using t-test. The difference was considered statistically significant when p-value fell below 0.05.

Following are examples that illustrate procedures for practicing the invention. These examples should not be construed as limiting.

Example 1

Set-Up of the Ultrasound-Enhanced Transscleral Delivery System

This Example provides specific embodiments of the ultrasound-enhanced transscleral delivery system. As shown in FIG. 1, the ultrasound transducer (20 kHz-2.5 MHz) is located on the exposed part of sclera. A well containing ultrasound transmitting medium (which may or may not contain drug molecules) is positioned on the sclera and the ultrasound transducer is immersed in the pharmaceutical solution/gel. Preferably, the ultrasound transducer is positioned from 0.5 mm to 5 mm above the targeted zone of the sclera and is immersed in the pharmaceutical solution/gel. Ultrasound is applied for about 30 seconds—about 5 minutes, and the power of the ultrasound is below 4 W/cm$^2$.

In another embodiment, the ultrasound-generating device is positioned around the limbus (FIG. 2). In another embodiment, the ultrasound-generating device is positioned in the cul-de-sac (FIG. 3). Additionally and alternatively, the ultrasound-generating device is positioned at the posterior segment of the eye (FIG. 4).

Subsequent of ultrasound application, the well containing the pharmaceutical solution/gel is placed in contact with the application site for a period of time (<30 min) to enable the drugs to penetrate the sclera.

Example 2

Enhancement of Delivering Macromolecules into Sclera by Ultrasound

Figure 5:
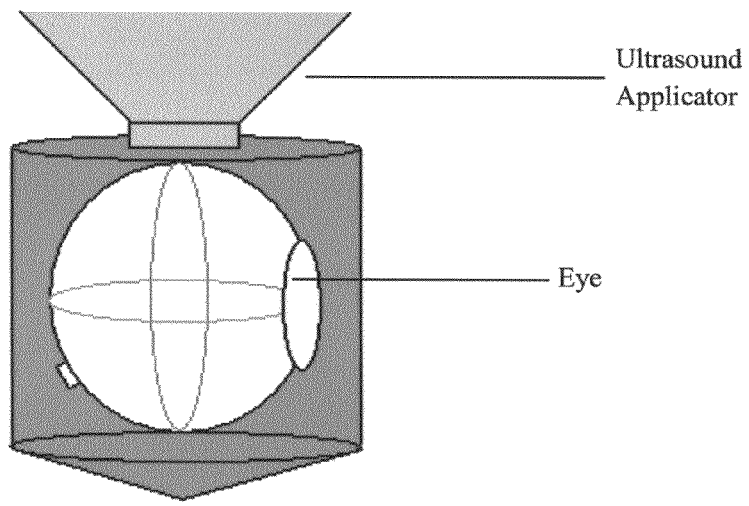
FIG. 5 is a schematic diagram illustrating the set up of in vitro experiments.

This Example demonstrates that the application of low frequency ultrasound for a short duration according to the present invention enhances delivery of macromolecules into intrascleral space. In the first set of experiments, the parameters of the ultrasound used were set as follows: frequency: 1 MHz, power: 0.5 W/cm$^2$, application duration: 30 seconds, size of transducer: 1 cm$^2$. Freshly enucleated New Zealand White Rabbit eyes were used as an ex vivo eye model, and 65 kDa protein fluorescent albumin was used as the model macromolecule. Whole rabbit eyes were immersed in fluorescent albumin solution. The ultrasound transducer was placed at about 0.5 mm above the sclera as shown in FIG. 5. Ultrasound was applied for 30 s and then the eyes were kept in fluorescent albumin for 5, 15 or 30 minutes. For the control experiment, the eyes were immersed in fluorescent albumin for 15 minutes without ultrasound application. The eyes were then flash frozen in OCT (Optimum Cutting Temperature) medium with liquid nitrogen and sectioned in cryostat for further investigation.

Figure 8:
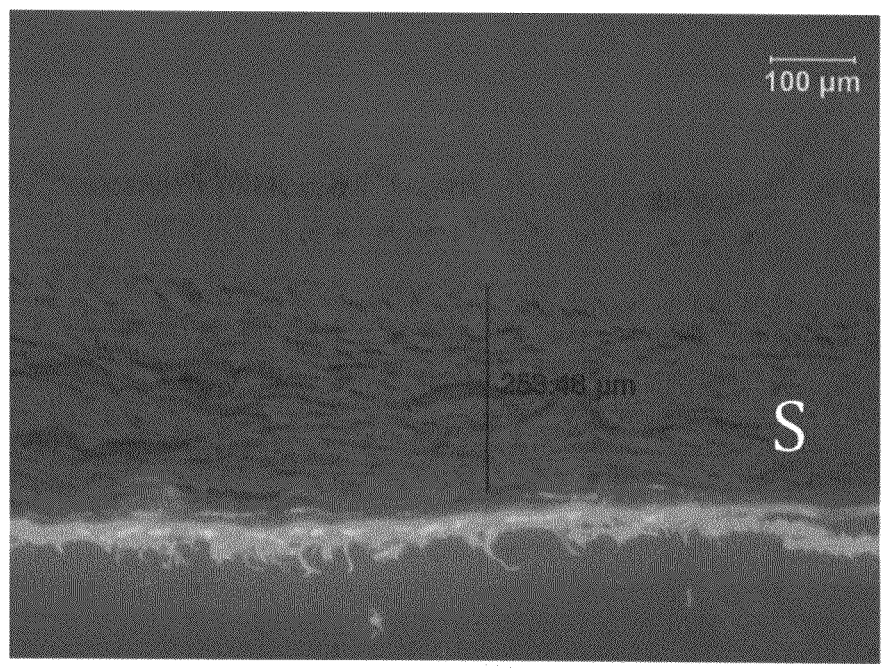
FIG. 8 shows the level of penetration in control experiment without ultrasound application. Fluorescent albumin was located outside the sclera and failed to penetrate into the sclera.
Figure 9:
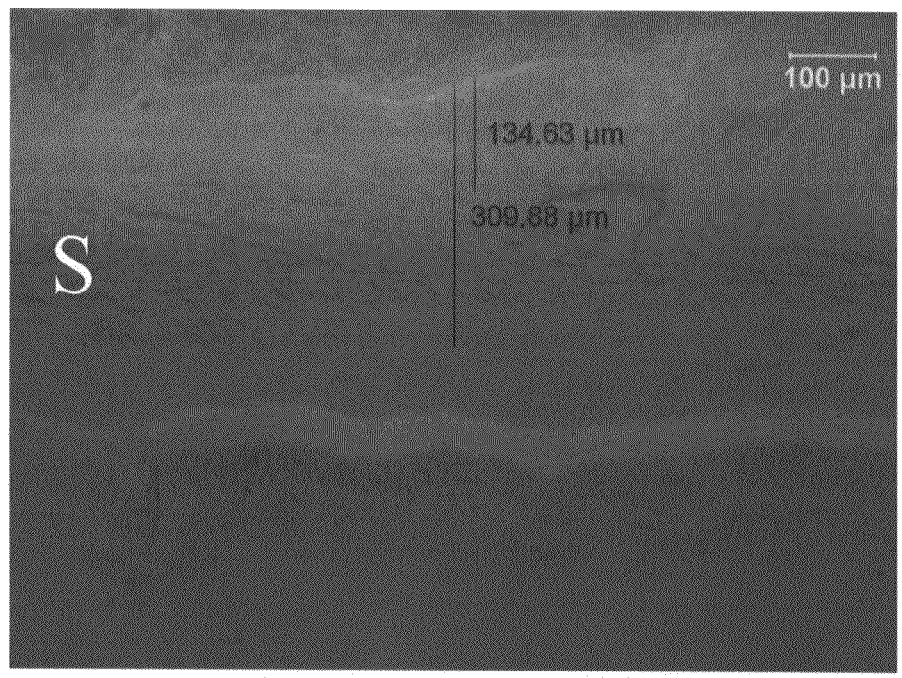
FIG. 9 shows the level of penetration in ultrasound experiment where immersion time was 15 minutes. Fluorescent albumin was penetrated into the deeper part of the sclera.

The results showed that after 30 seconds ultrasound application followed by 5-minute immersion, the percentage of depth of protein penetration into sclera increased 4 folds, from about 3% (FIG. 8, control) to about 13% (FIG. 13), as compared to the control in which no ultrasound was applied. The percentage of depth of protein penetration further increased from about 3% to about 35% (FIG. 9) after 15 minutes immersion, while there was no significant difference in percentage of depth of protein penetration between 15-minute and 30-minute immersion. The results revealed that the channels created were closed in 15 minutes after ultrasound application.

Figure 15A:
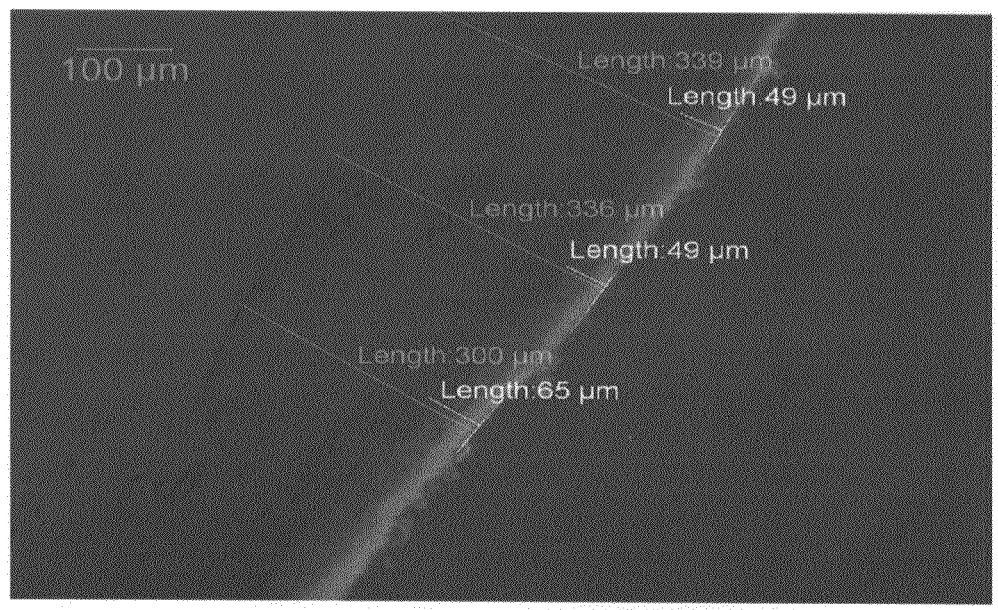
FIG. 15 shows the effect of ultrasound on the intrascleral penetration of FITC-BSA. Representative cryosections illustrate the protein penetration into the rabbit sclera: a) harvested from the control eye with no ultrasound treatment; b) harvested from the eye that was exposed to 30 s of ultrasound at 1 MHz and 0.5 W/cm$^2$. In both a) and b), eyes were immersed in the protein solution for 15 minutes. The green color is from the fluorescent tag of the protein. S: sclera; O: orbital side; U: uveal side. The mean and standard deviation are shown in (c), averaging from over 60 measurements and 3 eyes for each condition. (*p<0.05)
Figure 15B:
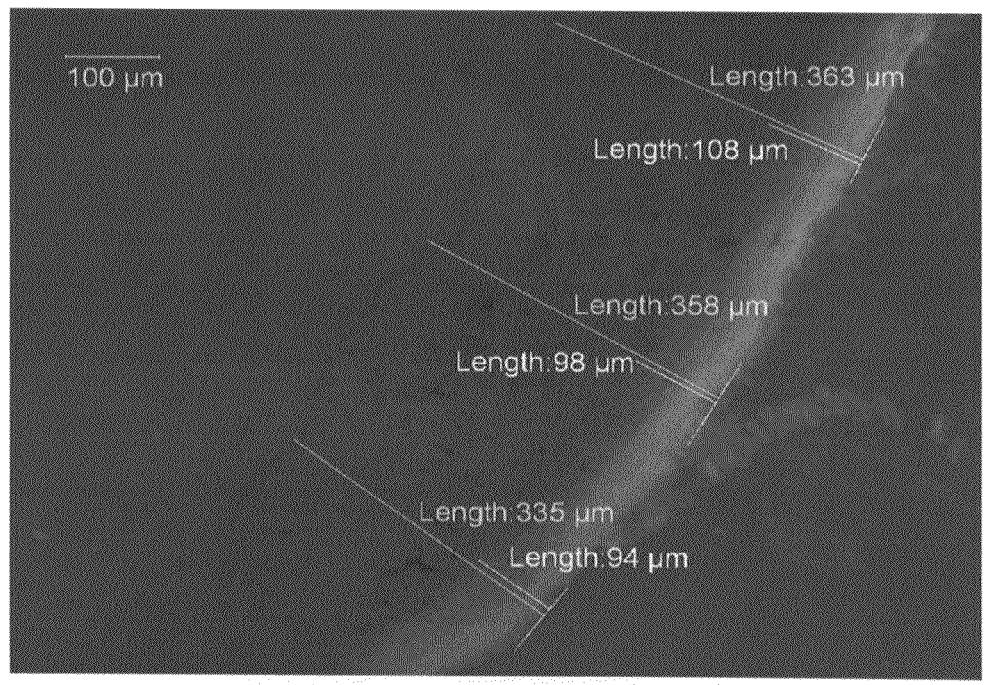
Figure 15C:
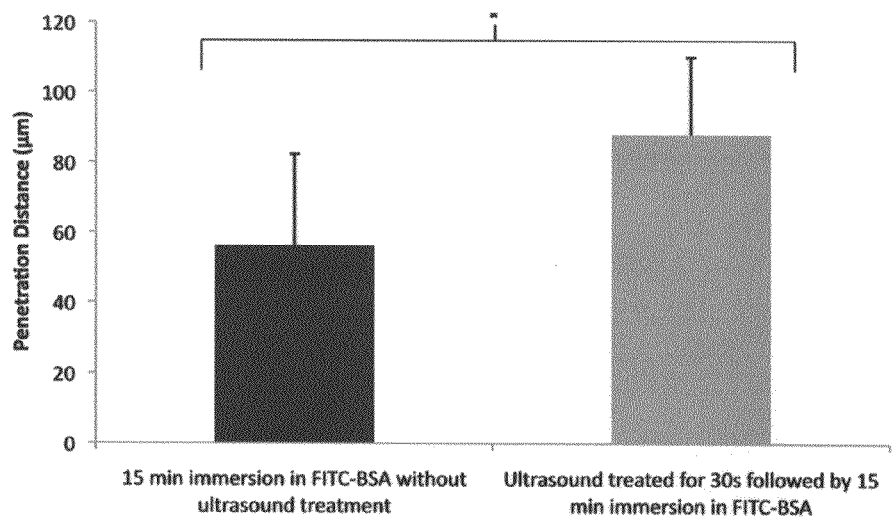

In another set of experiments, the effects of ultrasound on intrascleral protein transport and the depth of intrascleral penetration by ultrasound were further investigated. The results showed that the penetration distance of FITC-BSA was measured after cryo-sectioning the ocular tissues. FIG. 15 compares the results with and without ultrasound after the eyes were immersed in protein solution for 15 minutes. Representative cryo-sections are shown. The mean and standard deviation for each condition in the bar chart were obtained from over 60 measurements in three eyes. In the absence of ultrasound, FITC-BSA penetrated to 56.3±26.1 μm by passive diffusion, which was 19% of the thickness of the sclera. (The full thickness of the rabbit sclera was found to be 301.7±26.1 μm from averaging the measurements of 56 sclera sections.) A brief application (30 s) of low-power ultrasound increased the penetration distance to 88.0±22.0 μm, which was 29% of the thickness of the sclera. The difference in the intrascleral penetration was statistically significant (p<0.05).

Example 3

The Enhancement of Intrascleral Delivery by Cavitation

This Example demonstrates that the present invention enhances intrascleral delivery of therapeutic agents by cavitation not convection. Briefly, the parameters of the ultrasound were set as follows: frequency: 1 MHz, power: 0.5 W/cm$^2$, application duration: 30 seconds, size of transducer: 1 cm$^2$. Freshly enucleated New Zealand White Rabbit eyes were used as an ex viva eye model, and 65 kDa protein fluorescent albumin was used as the model macromolecule. The rabbit eyes were immersed in fluorescent albumin solution. After 30 seconds of ultrasound application at 1 MHz, the eyes were immediately flash frozen so that there was no time for the albumin to diffuse into the sclera.

Figure 10:
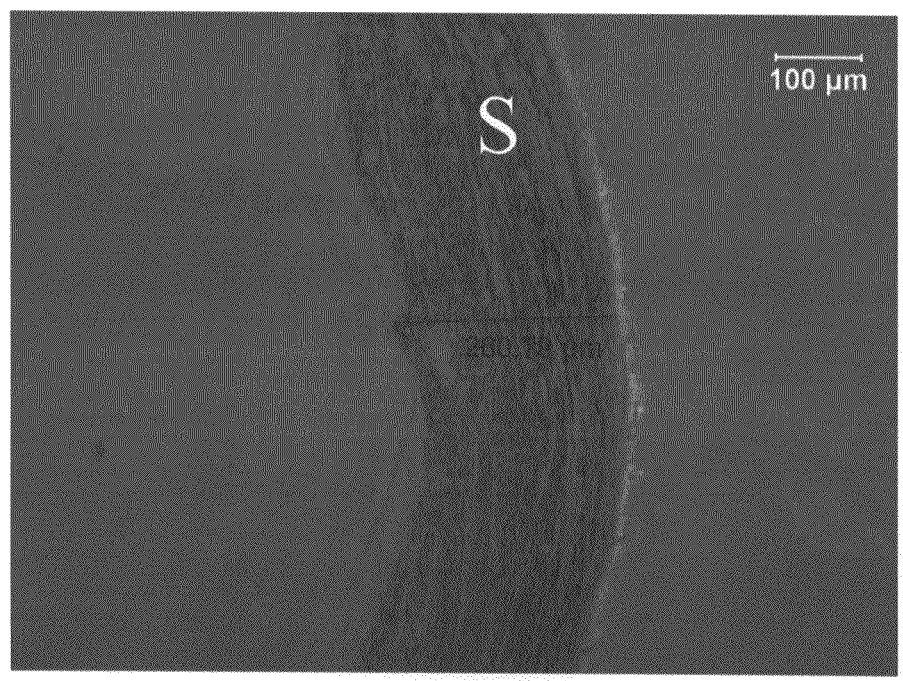
FIG. 10 shows the level of penetration when the eye is immediately frozen in O.C.T after 30-second ultrasound application such that the diffusion of fluorescent albumin is hindered. The level of penetration of this experiment is similar to that of the control, indicating that the covective effect of ultrasound is negligible in this method.

The results showed that the penetration depth was similar to that of the control (without ultrasound application) (FIG. 10), indicating that the effect of convection was very limited. Therefore, the enhancement of intrascleral delivery is due to cavitation, possibly by creating channels for large molecules to diffuse through, rather than the convective effect mediated by the ultrasonic wave itself. Preferably, the medium containing the drug molecules is placed in contact with the sclera for a period of time to allow drug diffusion after the ultrasound application.

Example 4

Localized Ultrasonic Cavitation Effect on Sclera

Figure 11:
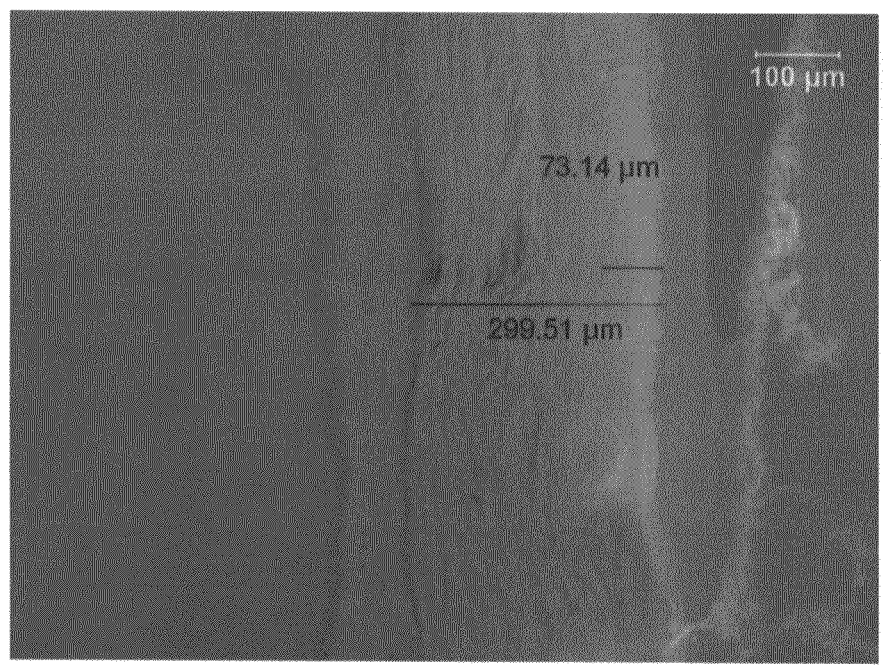
FIG. 11 shows the level of penetration in the zone of sclera where 30-second ultrasound is applied. After immersing in fluorescent albumin for 15 minutes, the fluorescent albumin penetrates in around 30% of the sclera.
Figure 12:
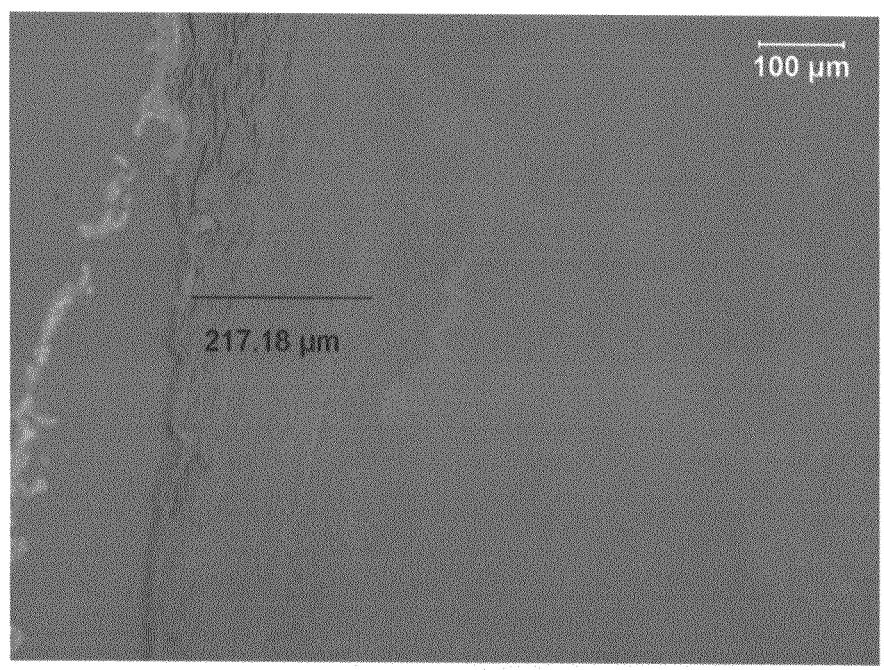
FIG. 12 shows the level of penetration in the zone of sclera which is opposite to the zone where ultrasound is applied (same experiment as FIG. 11). Little penetration of fluorescent albumin is observed.

This Example demonstrates that the present invention method can create localized effect on sclera. In the first set of experiments, rabbit eyes were treated with ultrasound for 30 seconds and then immersed in fluorescent albumin for 15 minutes. The results, as shown in FIG. 11, revealed that the effect of ultrasound was localized. The penetration of fluorescent albumin was increased to around 30% of the side of sclera treated with ultrasound; while, there was little penetration of fluorescent albumin on the opposite side of the sclera (FIG. 12).

In another set of experiments, the role of convection was assessed by measuring protein penetration during the application of ultrasound. To minimize the time for diffusion, the eye was frozen immediately after the ultrasound treatment. The results showed that FITC-BSA was found to stay near the scleral surface (FIG. 18), with a negligible penetration depth of 15.8±5.7 μm. This was in contrast to the much deeper penetration that occurred when time was given for diffusion after the ultrasound application (FIG. 15b).

Example 5

Enhancement of Intrascleral Diffusivity by Ultrasound Application

This Example demonstrates that the present invention enhanced intrascleral diffusivity. When the penetration distance was plotted against the square root of time, linear graphs were obtained, supporting that diffusion was the dominated mode of transport (FIG. 19) (35). Intrascleral diffusivity at 37° C. was calculated from the slopes of the graphs. In the first 15 minutes, the diffusivity of FITC-BSA was increased by 1.6 times as a result of ultrasound treatment, from $3.90 \times 10^8$ $cm^2/sec$ to $6.17 \times 10^{-8}$ $cm^2/sec$. Consistent with the observation that ultrasound effect was temporary (FIG. 16), the slope measuring the protein diffusivity was flattened after 15 min. Using the data from 15 min to 60 min post ultrasound, the intrascleral diffusivity of FITC-BSA was calculated to be $4.18 \times 10^{-8}$ $cm^2/sec$. This value is similar to the diffusivity without ultrasound treatment.

Example 6

The Increase in Scleral Permeability After Ultrasound Application is Temporary

Figure 13:
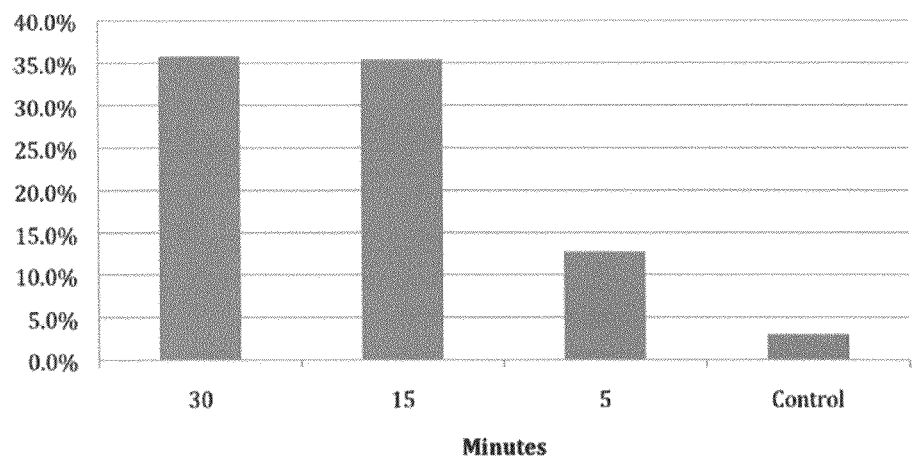
FIG. 13 shows the enhancement of fluorescent protein delivery in sclera after 30-second ultrasound application

This Example investigated the mechanism underlying the ultrasound-enhanced intrascleral protein transport, and demonstrates that the present invention creates a temporary increase in scleral permeability. In the first set of experiments, rabbit eyes were immersed in fluorescent albumin after ultrasound treatment at various time intervals. The results showed that the depth of penetration by albumin differed little between 15-minute and 30-minute immersion (FIG. 13). This indicated that the penetration effect of ultrasound is temporary and the channels created by cavitation are closed 15 minutes after ultrasound application.

Figure 14:
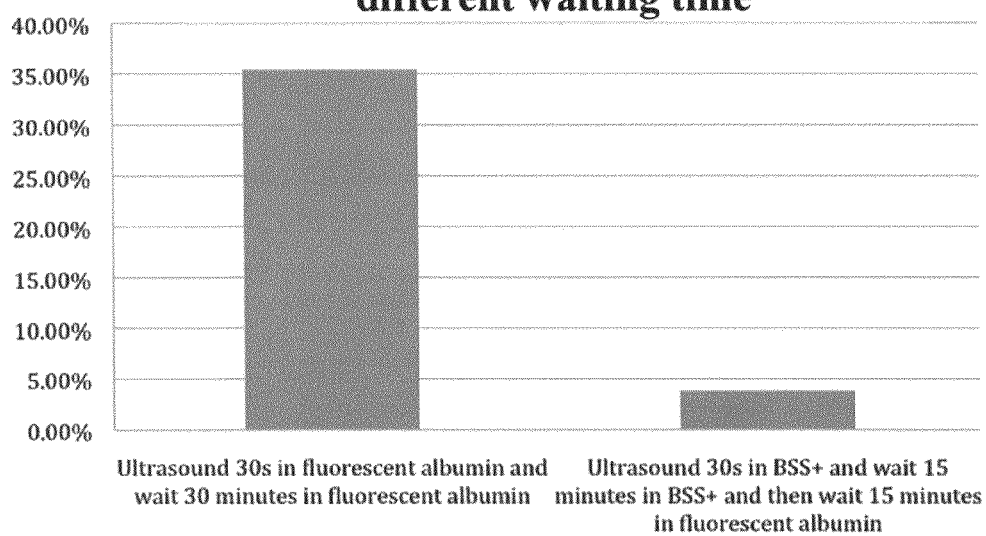
FIG. 14 shows the recovery of sclera at 15 minutes after 30-second ultrasound application.

In another set of experiments, rabbit eyes were immersed in BSS+, a non-fluorescent saline for human eye surgery, during ultrasound application as well as 15 minutes afterwards. After that, the eyes were transferred to fluorescent albumin solution and waited for 15 minutes. The results showed that for the eyes pre-treated with BSS+, the penetration was much lower, as compared to the sample without 15-minute BSS+ pretreatment, while the penetration of the BSS+ pre-treated eyes was similar to that of the control in Example 2 (FIG. 14). This reveals that the channels created by cavitation are closed in 15 minutes or less after ultrasound application. Once the channels are closed, macromolecules can no longer diffuse into the sclera. Thus, the penetration effect of ultrasound is temporary. As a result, the ultrasound treatment of the present invention has no permanent damage to the sclera structure.

In another set of experiments, the results showed that there appeared to be a short time window in which the sclera permeability for protein was improved by ultrasound. Briefly, the ultrasound-treated eye was first immersed in a colorless buffer for 15 minutes before placing it in the FITC-BSA solution. If the effect of ultrasound halts after 15 minutes, the protein penetration distance is expected to resemble the control without ultrasound. Indeed, no significant difference was observed between the ultrasound-treated and the control eye ($p=0.34$, FIG. 16).

Example 7

The Increase in Scleral Permeability by Ultrasound Application is Repeatable

This Example demonstrates that the enhancement in scleral permeability by the present invention is repeatable. The results, as shown in FIG. 17, revealed the penetration distance of FITC-BSA at 15 minutes after the eyes were exposed to first and second ultrasound treatment. (Fifteen minutes were lapsed between the two ultrasound applications.) The intrascleral penetration distance was comparable between the two cases ($p=0.21$).

Example 8

The Effect of the Low-Frequency Ultrasound Application on Ocular Tissues

This Example demonstrates that the present low-frequency ultrasound application does not cause harm to ocular tissues. In the first set of experiments, the contribution of thermal effects was gauged by the increase in temperature on the scleral surface. The results showed that the rise was less than 0.5° C. under the current operating conditions. Hence, the present invention generates negligible heat in ocular tissues.

Another set of experiments is performed to assess if ultrasound application causes any structural damage to the retina. Cryostat sections of both the normal and ultrasound-treated eyes were stained with H&E and examined under a microscope (FIG. 20). The results showed that there was no apparent difference between the two eyes in regard to both the sclera and the retina. Moreover, the ultrasound treatment did not seem to cause retina detachment or deformation of the retinal layer at the area of the treated zone.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

References

1. J. Park et al., Journal of Controlled Release 105, 279 (July, 2005).
2. S. S. Chrai, M. C. Makoid, S. P. Eriksen, J. R. Robinson, J Pharm Sci 63, 333 (March, 1974).
3. J. W. Sieg, J. R. Robinson, J Pharm Sci 65, 1816 (December, 1976).
4. R. D. Schoenwald, G. S. Deshpande, D. G. Rethwisch, C. F. Bartknecht, Journal of Ocular Pharmacology and Therapeutics 13, 41 (February, 1997).
5. D. M. Maurice, Survey of Opthalmology 47 Suppl 1, S41 (August, 2002).
6. J. Ambati et al., Invest Opthalmol Vis Sci 41, 1181 (April, 2000).
7. V. P. Ranta, A. Urtti, Adv Drug Deliv Rev 58, 1164 (Nov. 15, 2006).
8. A. Urtti, Adv Drug Deliv Rev 58, 1131 (Nov. 15, 2006).
9. S. Mitragotri, D. Blankschtein, R. Langer, Science 269, 850 (August, 1995).
10. N. P. Katz, D. E. Shapiro, T. E. Herrmann, J. Kost, L. M. Custer, Anesth Analg 98, 371 (February, 2004).
11. P. Santoianni, M. Nino, G. Calabro, Deiuiatol Online J 10, 24 (2004).
12. V. Zderic, S. Vaezy, R. W. Martin, J. I. Clark, Ultrasound Med Biol 28, 823 (June, 2002).
13. V. Zderic, J. I. Clark, S. Vaezy, J Ultrasound Med 23, 1349 (October, 2004).
14. V. Zderic, J. I. Clark, R. W. Martin, S. Vaezy, Cornea 23, 804 (November, 2004).
15. V. H. Lee, J. R. Robinson, J Ocul Pharmacol 2, 67 (Winter, 1986).
16. D. H. Geroski, H. F. Edelhauser, Advanced Drug Delivery Reviews 52, 37 (Oct. 31, 2001).
17. M. E. Myles, D. M. Neumann, J. M. Hill, Adv Drug Deliv Rev 57, 2063 (Dec. 13, 2005).
18. K. G. Janoria, S. Gunda, S. H. Boddu, A. K. Mitra, Expert Opinion on Drug Delivery 4, 371 (July, 2007).
19. S. Mitragotri, J. Kost, Adv Drug Deliv Rev 56, 589 (Mar. 27, 2004).
20. H. Kourlas and P. Abrams. Ranibizumab for the treatment of neovascular age-related macular degeneration: A review. Clinical Therapeutics 29: 1850-1861 (2007).
21. M. Zarbin and B. Szirth. Current treatment of age-related macular degeneration. Optometry and Vision Science 84: 559-572 (2007).
22. P. A. Sieving, R. C. Caruso, W. Tao, H. R. Coleman, D. J. Thompson, K. R. Fullmer, and R. A. Bush. Ciliary neurotrophic factor (CNTF) for human retinal degeneration: phase I trial of CNTF delivered by encapsulated cell intraocular implants. Proc Natl Acad Sci USA 103: 3896-901 (2006).
23. V. H. Lee and J. R. Robinson. Topical ocular drug delivery: recent developments and future challenges. J Ocul Pharmacol 2: 67-108 (1986).
24. J. Ambati, C. S. Canakis, J. W. Miller, E. S. Gragoudas, A. Edwards, D. J. Weissgold, I. Kim, F. C. Delon, and A. P. Adamis. Diffusion of high molecular weight compounds through sclera. Investigative Opthalmology & Visual Science 41: 1181-1185 (2000).
25. J. Jiang, J. S. Moore, H. F. Edelhauser, and M. R. Prausnitz. Intrascleral drug delivery to the eye using hollow microneedles. Pharm Res 26: 395-403 (2009).
26. M. Barza, C. Peckman, and J. Baum. Transscleral iontophoresis of cefazolin, ticarcillin, and gentamicin in the rabbit. Opthalmology 93: 133-9 (1986).
27. D. M. Maurice. Iontophoresis of fluorescein into the posterior segment of the rabbit eye. Opthalmology 93: 128-32 (1986).
28. M. Barza, C. Peckman, and J. Baum. Transscleral iontophoresis of gentamicin in monkeys. Invest Opthalmol Vis Sci 28: 1033-6 (1987).
29. T. Asahara, K. Shinomiya, T. Naito, and H. Shiota. Induction of gene into the rabbit eye by iontophoresis: preliminary report. Jpn J Opthalmol 45: 31-9 (2001).
30. M. Voigt, Y. de Kozak, M. Halhal, Y. Courtois, and F. Behar-Cohen. Down-regulation of NOSII gene expression by iontophoresis of anti-sense oligonucleotide in endotoxin-induced uveitis. Biochem Biophys Res Commun 295: 336-41 (2002).
31. T. M. Parkinson, E. Ferguson, S. Febbraro, A. Bakhtyari, M. King, and M. Mundasad. Tolerance of ocular iontophoresis in healthy volunteers. J Ocul Pharmacol Ther 19: 145-51 (2003).
32. F. B. Kremer, P. Walton, and G. Gensheimer. Determination of corneal thickness using ultrasonic pachometry. Am Opthalmol 17: 506-7 (1985).
33. M. L. McDermott, J. E. Puklin, G. W. Abrams, and D. Eliott. Phacoemulsification for cataract following pars plana vitrectomy. Ophthalmic Surg Lasers 28: 558-64 (1997).
34. C. J. Pavlin, K. Harasiewicz, M. D. Sherar, and F. S. Foster. Clinical use of ultrasound biomicroscopy. Opthalmology 98: 287-95 (1991).
35. W. M. Salzman. Drug Delivery—Engineering Principles for Drug Therapy, Oxford University Press, Inc., New Work, 2001.
36. K. M. Hamalainen, K. Kananen, S. Auriola, K. Kontturi, and A. Urtti. Characterization of paracellular and aqueous penetration routes in cornea, conjunctiva, and sclera. Invest Opthalmol Vis Sci 38: 627-34 (1997).
37. A. Edwards and M. R. Prausnitz. Fiber matrix model of sclera and corneal stroma for drug delivery to the eye. Aiche Journal 44: 214-225 (1998).
38. S. H. Kim, R. J. Lutz, N. S. Wang, and M. R. Robinson. Transport barriers in transscleral drug delivery for retinal diseases. Ophthalmic Res 39: 244-54 (2007).
39. G. Merino, Y. N. Kalia, and R. H. Guy. Ultrasound-enhanced transdermal transport. J Pharm Sci 92: 1125-37 (2003).
40. A. Blinc, C. W. Francis, J. L. Trudnowski, and E. L. Carstensen. Characterization of ultrasound-potentiated fibrinolysis in vitro. Blood 81: 2636-43 (1993).
41. J. V. Braaten, R. A. Goss, and C. W. Francis. Ultrasound reversibly disaggregates fibrin fibers. Thromb Haemost 78: 1063-8 (1997).
42. F. Perren, J. Loulidi, D. Poglia, T. Landis, and R. Sztajzel. Microbubble potentiated transcranial duplex ultrasound enhances IV thrombolysis in acute stroke. J Thromb Thrombolysis 25: 219-23 (2008).
43. J. Collis, R. Manasseh, P. Liovic, P. Tho, A. Ooi, K. Petkovic-Duran, and Y. Zhu. Cavitation microstreaming and stress fields created by microbubbles. Ultrasonics 50: 273-279.
44. K. S. Suslick. Ultrasound: its chemical, physical, and biological effects, VCH Publishers, New York, 1988.

45. J. P. L. Timothy J. Mason. *Sonochemistry: theory, applications and uses of ultrasound in chemistry*, Ellis Horwood, Chichester, 1988.
46. T. Kodama and Y. Tomita. Cavitation bubble behavior and bubble-shock wave interaction near a gelatin surface as a study of in vivo bubble dynamics. *Applied Physics B-Lasers and Optics* 70: 139-149 (2000).
47. M. A. Qasim and A. Salahuddin. The conformational consequences of maleylation of amino groups in ovalbumin. *J Biochem* 85: 1029-35 (1979).
48. P. G. Watson and R. D. Young. Scleral structure, organisation and disease. A review. *Exp Eye Res* 78: 609-23 (2004).
49. E. D. Hay. *Cell biology of extracellular matrix*, Plenum Press, New York, 1981.
50. H. Yokoi, T. Kinoshita, and S. Zhang. Dynamic reassembly of peptide RADA16 nanofiber scaffold. *Proc Natl Acad Sci USA* 102: 8414-9 (2005).
51. I. Lavon and J. Kost. Ultrasound and transdermal drug delivery. *Drug Discovery Today* 9: 670-6 (2004).
52. M. Rockville. Information for Manufacturers Seeking Marking Clearance of Diagnostic Ultrasound Systems and Transducers. In F. a. D. Administration (ed) (F. a. D. Administration, ed), Center for Devices and Radiological Health, 1997.
53. L. P. J. Cruysberg, R. M. M. A. Nuijts, D. H. Geroski, J. A. Gilbert, F. Hendrikse, and H. F. Edelhauser. The influence of intraocular pressure on the transscleral diffusion of high-molecular-weight compounds. *Investigative Opthalmology & Visual Science* 46: 3790-3794 (2005).

We claim:

1. An ultrasound-enhanced method for delivering one or more therapeutic agents to a target site in intrascleral space or across the sclera to intraocular tissue, comprising:
    a) providing an ultrasound-generating device and a well for transmitting ultrasound;
    b) positioning the ultrasound-generating device and the well so that ultrasound will be directed to a desired site of a sclera;
    c) generating ultrasound using the ultrasound-generating device and applying the ultrasound to the desired site of the sclera, wherein the ultrasound is applied at a frequency of about 20 kHz to about 100 kHz, wherein the ultrasound is applied at least once; and
    d) providing a therapeutic agent to the desired site of the sclera before, during, or after the ultrasound is applied; wherein said method delivers the therapeutic agent having a molecular weight of up to 150 k Dalton to a target site in intrascleral space or across the sclera to intraocular tissue.

2. The method according to claim 1, wherein the ultrasound is applied at a frequency of about 20 kHz to about 40 kHz.

3. The method according to claim 1, wherein the ultrasound is applied at a power of no greater than about 4 W/cm$^2$.

4. The method according to claim 1, wherein the ultrasound application does not increase temperature of the scleral surface more than by about 1° C.

5. The method according to claim 1, wherein the ultrasound is applied as continuous or pulsating waves.

6. The method according to claim 5, wherein the ultrasound is applied as pulsating waves with duty cycle ranging from about 10% to about 90%.

7. The method according to claim 1, wherein the therapeutic agent is delivered to the target site by applying the ultrasound to the desired site of the sclera for less than about 5 minutes.

8. The method according to claim 1, wherein the ultrasound is applied to the desired site of the sclera multiple times with a period of time lapse of at least about 1 minute each time.

9. The method according to claim 1, wherein the ultrasound application creates one or more temporary channels in the eye.

10. The method according to claim 1, wherein the therapeutic agent is delivered via microcarriers or nanocarriers selected from the group consisting of microbubbles, microparticles, liposomes, polymeric micelles, polymeric vesicles, polymeric particles, protein particles, peptide nanoparticles, nanospheres, nanodendrimers, nanocolloids, nanodots, nanocolumns, and any combination thereof.

11. The method according to claim 1, wherein the therapeutic agent provided remains in contact with the desired site of the sclera for up to about 30 minutes after the ultrasound application.

12. The method according to claim 1, used for treating a disease or a condition selected from the group consisting of choroidal neovascularization, age-related macular degeneration, diabetic retinopathy, glaucoma, retinitis pigmentosa, macular edema, macular degeneration, multirecurrent pterygia, ocular toxoplasmosis, proliferative vitreoretinopathy (PVR), Stevens-Johnson syndrome (SJS), ocular cicatricial pemphigoid (OW), an ocular degenerative condition, a post-surgery condition, an ocular tissue injury, ocular tumor, and any combination thereof.

13. The method according to claim 1, wherein the target site is selected from intrascleral space or intraocular tissue selected from vitreous humor, retina, choroid, or optic nerve tissue.

14. The method according to claim 1, wherein the therapeutic agent is delivered to the target site by applying the ultrasound to the desired site of the sclera for less than about 2 minutes for each application.

15. The method according to claim 2, wherein the ultrasound is applied at a power of no greater than about 0.5 W/cm$^2$.

16. The method according to claim 2, wherein the ultrasound is applied at a frequency of about 40 kHz.

17. The method according to claim 1, wherein the ultrasound is applied to the desired site of the sclera at least two times.

18. The method according to claim 17, wherein each ultrasound is applied with a period of time lapse of at least about 5 minutes between applications.

19. The method, according to claim 1, wherein the therapeutic agent has a molecular weight of higher than 5,000 Dalton, and wherein the therapeutic agent is delivered to a target site in intrascleral space or across the sclera to intraocular tissue.

* * * * *